US007026343B2

(12) United States Patent
Prochownik et al.

(10) Patent No.: US 7,026,343 B2
(45) Date of Patent: Apr. 11, 2006

(54) PHARMACOLOGIC INHIBITION OF MYC FUNCTION

(75) Inventors: Edward V. Prochownik, Pittsburgh, PA (US); Christine Giap, Pittsburgh, PA (US); John S. Lazo, Pittsburgh, PA (US); Xiaoying Yin, Chapel Hill, NC (US)

(73) Assignee: University of Pittsburgh - of the Commonwealth System of Higher Education, Pittsburgh, PA (US)

( * ) Notice: Subject to any disclaimer, the term of this patent is extended or adjusted under 35 U.S.C. 154(b) by 120 days.

(21) Appl. No.: 10/459,769

(22) Filed: Jun. 12, 2003

(65) Prior Publication Data

US 2004/0034060 A1    Feb. 19, 2004

Related U.S. Application Data

(60) Provisional application No. 60/388,414, filed on Jun. 12, 2002.

(51) Int. Cl.
*A61K 31/41*    (2006.01)
*A61K 31/655*    (2006.01)
*A61K 31/52*    (2006.01)
*A61K 31/505*    (2006.01)
*A61K 31/40*    (2006.01)

(52) U.S. Cl. ...................... 514/370; 514/150; 514/364; 514/369; 514/424; 514/654

(58) Field of Classification Search ................ 514/370, 514/150, 369, 364, 424, 654
See application file for complete search history.

(56) References Cited

OTHER PUBLICATIONS

Nupponen, Nina N., Kakkola, Laura, Koivisto, Pasi and Visakorpi, Tapio, "Genetic Alterations in Hormone-Refractory Recurrent Prostate Carcinomas," *American Journal of Pathology*, vol. 153, No. 1, pp. 141-148 (Jul. 1998).
Langlands, Kenneth and Prochownik, Edward V., "A Rapid Method for the Preparation of Yeast Lysates That Facilitates the Immunodetection of Proteins Generated by the Yeast Two-Hybrid System," *Analytical Biochemistry*, vol. 249, pp. 250-252 (1997).
Bazarov, Alex V., et al., "A Modest Reduction in c-Myc Expression Has Minimal Effects on Cell Growth and Apoptosis But Dramatically Reduces Susceptibility to Ras and Raf Transformation," *Cancer Research*, vol. 61, pp. 1178-1186 (Feb. 1, 2001).
Yin, Xiao-Ying, et al., "Inverse Regulation of Cyclin B1 by c-Myc and p53 and Induction of Tetraploidy by Cyclin B1 Overexpression," *Cancer Research*, vol. 61, pp. 6487-6493 (Sep. 1, 2001).

Jenkins, Robert B., Qian, Junqi, Lieber, Michael M. and Bostwick, David G., "Detection of c-myc Oncogene Amplification and Chromosomal Anomalies in Matastatic Prostatic Carcinoma by Fluorescence in Situ Hybridization," *Cancer Research*, vol. 57, pp. 524-531 (Feb. 1, 1997).
Kimura, Shinya, Maekawa, Taira, Hirakawa, Kouichi, Murakami, Akira and Abe, Tatsuo, "Alterations of c-myc Expression by Antisense Oligodeoxynucleotides Enhance the Induction of Apoptosis in HL-60 Cells," *Cancer Research*, vol. 55, pp. 1379-1384 (Mar. 15, 1995).
Nesbit, Chadd E., Grove, Linette E., Yin, Xiaoying and Prochownik, Edward V., "Differential Apoptotic Behaviors of c-myc, N-myc, and L-myc Oncoproteins," *Cell Growth & Differentiation*, vol. 9, pp. 731-741, (Sep. 1998).
Mateyak, Maria K., Obaya, Alvaro J., Susumu and Sedivy, John M., "Phenotypes of c-Myc-Deficient Rat Fibroblasts Isolated by Targeted Homologous Recombination," *Cell Growth & Differentiation*, vol. 8, pp. 1039-1048 (Oct. 1997).
Bowlin, Terry L., McKown, Brenda J. and Sunkara Prasad S., "Ornithine Decarboxylase Induction and Polyamine Biosynthesis Are Required for the Growth of Interleukin-2- and Interleukin-3-Dependent Cell Lines," *Cellular Immunology*, vol. 98, pp. 341-350 (1986).
Prochownik, Edward V., Grove, Linette Eagle, Deubler, Debra, et al., "Commonly Occuring Loss and Mutation of the MXI1 Gene in Prostate Cancer," *Genes, Chromosomes & Cancer*, vol. 22, pp. 295-304 (1998).
Davis, Ann C., Wims, Marie, Spotts, Gerald D., Hann, Stephen R. and Bradley, Allan, "A null c-myc mutation causes lethality before 10.5 days of gestation in homozygotes and reduced fertility in heterozygous female mice," *Genes & Development*, vol. 7, pp. 671-682 (1993).

(Continued)

*Primary Examiner*—Rebecca Cook
(74) *Attorney, Agent, or Firm*—Jesse A. Hirshman

(57) ABSTRACT

The c-Myc oncoprotein, a helix-loop-helix-leucine zipper (HLH-ZIP) transcription factor, is frequently deregulated in human cancers. All known functions of c-Myc, including those pertaining to transformation, require that it heterodimerize with another HLH-ZIP protein, Max. Using a high throughput yeast-based assay, we identified seven low molecular weight substances that inhibit c-Myc-Max association. Each compound also prevented this interaction in vitro and inhibited the growth of c-Myc-expressing fibroblasts, although not of fibroblasts lacking c-Myc. Finally, short-term exposure of c-Myc over expressing fibroblasts to several of the compounds markedly reduced their in vivo tumorigenicity. These studies suggest that yeast-based assays can be used to identify inhibitors of protein-protein interactions and that these frequently function in mammalian cells. The signature specificities of each of the c-Myc-Max compounds identified here further suggest synergistic in vivo function.

32 Claims, 10 Drawing Sheets

OTHER PUBLICATIONS

Shapiro, David N., Valentine, Virginia, Eagle, Linette, et al., "Assignment of the Human MAD and MXI1 Genes to Chromosomes 2p12-p13 and 10q24-q25," *Genomics*, vol. 23, pp. 282-286 (1994).

Steiner, Mitchell S., Anthony, Catherine T., Lu, Yi and Holt, Jeffrey T., "Antisense c-myc Retroviral Vector Suppresses Established Human Prostate Cancer," *Human Gene Therapy*, vol. 9, pp. 747-755 (Mar. 20, 1998).

Ge, Kai, Minhas, Farooq, Duhadaway, James, Mao, Nien-Chen, et al., "Loss of Heterozygosity and Tumor Suppressor Activity of BIN1 in Prostate Carcinoma," *Int. J. Cancer*, vol. 86, pp. 155-161, (2000).

Van Waardenburg, Robert C.A.M., Meijer, Coby, et al., "Effects of an Inducible Anti-Sense c-myc Gene Transfer in a Drug-Resistant Human Small-Cell Lung-Carcinoma Cell Line," *Int. J. Cancer*, vol. 73, pp. 544-550 (1997).

Yin, Xiaoying, Grove, Linnette, et al., "Myc Target in Myeloid Cells-1, a Novel c-Myc Target, Recapitulates Multiple c-Myc Phenotypes," *The Journal of Biological Chemistry*, vol. 277, No. 22, pp. 19998-20010, (May 31, 2002).

Langlands, Kenneth, Yin, Xiaoying, et al., "Differential Interactions of Id Proteins with Basic-Helix-Loop-Helix Transcription Factors," *The Journal of Biological Chemistry*, vol. 277, No. 32, pp. 19785-19793, (Aug. 8, 1997).

Zhang, Hong, Fan, Saijun and Prochownik, Edward V., "Distinct Roles of MAX Protein Isoforms in Proliferation and Apoptosis," *The Journal of Biological Chemistry*, vol. 272, No. 28, pp. 17416-17424, (Jul. 11, 1997).

DuHadaway, James B., Lynch, Frank J., et al., "Immunohistochemical Analysis of Bin1/Amphiphysin II in Human Tissues: Diverse Sites of Nuclear Expression and Losses in Prostate Cancer," *Journal of Cellular Biochemistry*, vol. 88, pp. 635-642 (2003).

Ebinuma, Hirotoshi, Saito, Hidetsugu, Kosuga, Motomichi, et al., "Reduction of c-myc Expression by an Antisense Approach under Cre/loxP Switching Induces Apoptosis in Human Liver Cancer Cells," *Journal of Cellular Physiology*, vol. 188, pp. 56-66 (2001).

Bai, Chang and Elledge, Stephen J., "Gene Identification Using the Yeast Two-Hybrid System," *Methods in Enzymology*, vol. 273, pp. 331-347 (1996).

Prochownik, Edward V., Kukowska, Jolanta and Rodgers, Claire, "c-myc Antisense Transcripts Accelerate Differentiation and Inhibit $G_1$ Progression in Murine Erythroleukemia Cells," *Molecular and Cellular Biology*, vol. 8, No. 9, pp. 3683-3695 (Sep. 1998).

Smith, Michael J., Charron-Prochownik, Denise C., et al., "The Leucine Zipper of c-Myc is Required for Full Inhibition of Erythroleukemia Differentiation," *Molecular and Cellular Biology*, vol. 10, No. 10, pp. 5333-5339 (Oct. 1990).

Freytag, Svend O., "Enforced Expression of the c-myc Oncogene Inhibits Cell Differentiation by Precluding Entry into a Distinct Predifferentiation State in $G_0/G_1$," *Molecular and Cellular Biology*, vol. 8, No. 4, pp. 1614-1624 (Apr. 1998).

Schreiber-Agus, Nicole, Meng, Yong, Hoang, Tin, et al., "Role of Mxi1 in ageing organ systems and the regulation of normal and neoplastic growth," *Nature*, vol. 393, pp. 483-487 (Jun. 4, 1998).

Auvinén, Merja, Paasineen, Aino, Andersson, Leif C. and Hölttä, Erkki, "Ornithine decarboxylase activity is critical for cell transformation," *Nature*, vol. 360, pp. 355-358 (Nov. 26, 1992).

O'Hagan, Rónán C., Schriber-Agus, Nicole, Chen, Ken, et al., "Gene-target recognition among members of the Myc superfamily and implications for oncogenesis," *Nature Genetics*, vol. 24, pp. 113-119 (Feb. 2000).

Eagle, Linette R., Yin, Xiaoying, Brothman, Arthur R., et al., "Mutation of the MXI1 gene in prostate cancer," *Nature Genetics*, vol. 9, pp. 249-255 (Mar. 1995).

Landolfi, Nicholas F., Yin, Xiao-Ming, Capra, J. Donald and Tucker, Phillip W., "A conserved heptamer upstream of the IgH promoter region octamer can be the site of a coordinate protein—DNA interaction," *Nucleic Acids Research*, vol. 16, No. 12, pp. 5503-5514 (1988).

Littlewood, Travor D., Hancock, David C., Danielian, Paul S., et al., "A modified oestrogen receptor ligand-binding domain as an improved switch for the regulation of heterologous proteins," *Nucleic Acids Research*, vol. 23, No. 10, pp. 1686-1690 (1995).

Yin, Xiao Ying, Grove, Linnette, Datta, Nabanita S., et al., "C-myc overexpression and p53 loss cooperate to promote genomic instability," *Oncogene*, vol. 18, pp. 1177-1184 (1999).

Nesbit, Chadd E., Tersak, Jean M. and Prochownik, Edward V., "MYC oncogenes and human neoplastic disease," *Oncogene*, vol. 18, pp. 3004-3016, (1999).

Yin, Xiao-Ying, Gupta, Kalpana, Han, Wei Ping, et al., "Mmip-2, a novel RING finger protein that interacts with mad members of the Myc oncoprotein network," *Oncogene*, vol. 18, pp. 6621-6634, (1999).

Luscher, Bernhard and Larsson, Lars-Gunnar, "The basic region/helix—loop—helix/leucine zipper domain of Myc proto-oncoproteins: Function and regulation," *Oncogene*, vol. 18, pp. 2955-2966, (1999).

Van Antwerp, Mary E., Chen, De Gao, Chang, Christina and Prochownik, Edward V., "A Point Mutation in the DyoD Basic Domain Imparts c-Myc-Like Properties," *Proc. Natl. Acad. Sci. USA*, vol. 89, No. 19, pp. 9010-9014 (Oct. 1, 1992).

Prochownik, Edward V. and Van Antwerp, Mary, "Differential patterns of DNA binding by myc and max proteins," *Proc. Natl. Acad. Sci. USA*, vol. 90, pp. 960-964 (Feb. 1993).

Bello-Fernandez, Concha, Packham, Graham and Cleveland, John L., "The ornithine decarboxylase gene is a transcriptional target of c-Myc," *Proc. Natl. Acad. Sci. USA*, vol. 90, pp. 7804-7808 (Aug. 1993).

Coller, Hilary A., Grandori, Carla, Tamayo, Pablo, Colbert, Trent, Lander, Eric S. and Eisenman, Robert N., "Expression analysis with oligonucleotide microarrays reveals that MYC regulates genes involved in growth, cell cycle, signaling, and adhesion," *Proc. Natl. Acad. Sci. USA*, vol. 97, No. 7, pp. 3260-3265 (Mar. 28, 2000).

Berg, Thorsten, Cohen, Steven B., Deshamais, Joel, et al., "Small-molecule antagonists of Myc/Max dimerization inhibit transformation of chicken embryo fibroblasts," *Proc. Natl. Acad. Sci. USA*, vol. 99, No. 6, pp. 3830-3835 (Mar. 19, 2002).

Bengal, Eyal, Flores, Osvaldo, Rangarajan, Pundi N., et al., Positive control mutations in the MyoD basic region fail to show cooperative DNA binding and transcriptional activation in vitro, *Proc. Natl. Acad. Sci. USA*, vol. 91, pp. 6221-6225 (Jun. 1994).

Wang, Jia-Lun, Liu, Dongxiang, Zhang, Zhi-Jia, et al., "Structure-based discovery of an organic compound that binds Bcl-2 protein and induces apoptosis of tumor cells," *Proc. Natl. Acad. Sci. USA*, vol. 97, No. 13, pp. 7124-7129 (Jun. 20, 2000).

Taj, Mary M., Tawil, Rana J., Engstrom, Lars D., et al., "Mxi1, a Myc Antagonist, Suppresses Proliferation of DU145 Human Prostate Cells," *The Prostate*, vol. 47, pp. 194-204 (2001).

Zhang, Xuejun, Lee, Chung, Ng, Po-Ying, et al., "Prostatic Neoplasia in Transgenic Mice with Prostate-Directed overexpression of the c-myc Oncoprotein," *The Prostate*, vol. 43, pp. 278-285 (2000).

Foster, Barbara A., Coffey, Heather A., Morin, Michael J., and Rastinejad, Farzan, "Pharmacological Rescue of Mutant p53 Conformation and Function," *Science*, vol. 286, pp. 2507-2510 (Dec. 24, 1999).

Jain, Meenakshi, Arvanitis, Constadina, Chu, Kenneth, et al., "Sustained Loss of a Neoplastic Phenotype by Brief Inactivation of MYC," *Science*, vol. 297, pp. 102-104 (Jul. 5, 2002).

Komarov, Pavel G., Komarova, Elena A., Kondratov, Roman V., et al., "A Chemical Inhibitor of p53 that Protects Mice from the Side Effects of Cancer Therapy," *Science*, vol. 285, pp. 1733-1737 (Sep. 1999).

Turner, Richard and Tjian, Robert, "Leucine Repeats and an Adjacent DNA Binding Domain Mediate the Formation of Functional cFos-cJun Heterodimers," *Science*, vol. 243, Issue 243, pp. 1689-1694 (Mar. 31, 1989).

Greene, D.R., Taylor, S.R., Aihara, M., Yoshida, K., et al., "DNA Ploidy and Clonal Selection in ras + myc-Induced Mouse Prostate Cancer," *Int. J. Cancer*, vol. 60, pp. 395-399 (1995).

Overview of ChemBridge Corporation and description of DIVERSet combinatorial library, available at ChemBridge website at http://chembridge.com/chembridge/index_large.html, Jan. 7, 2004.

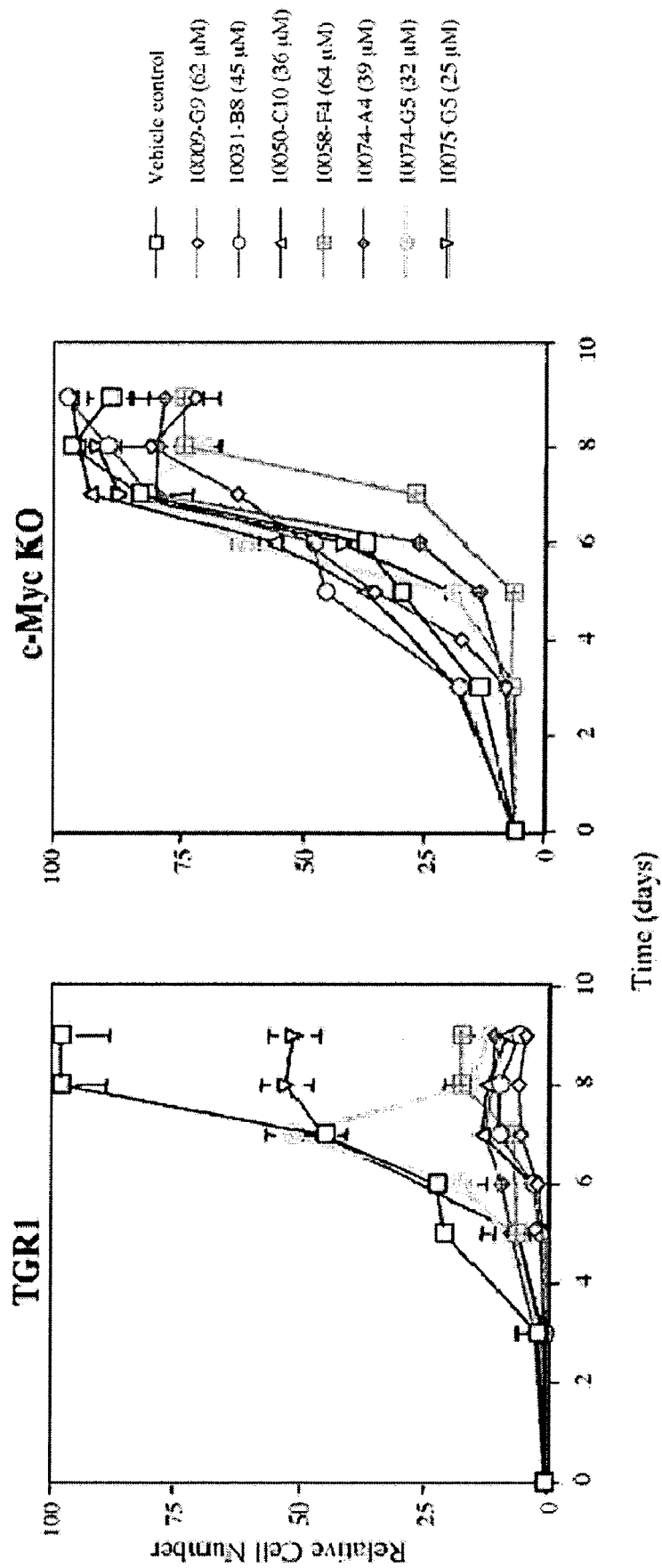

PHARMACOLOGIC INHIBITION OF MYC FUNCTION

CROSS REFERENCE TO RELATED APPLICATIONS

This application claims priority under 35 U.S.C. § 119(e) to U.S. Provisional Patent Application No. 60/388,414, filed Jun. 12, 2002, which is incorporated herein by reference in its entirety.

STATEMENT REGARDING FEDERAL SUPPORT

This work was supported by DOD Grant DAMD 17-00-1-0013 and NIH grant HL 33741.

BACKGROUND

1. Field of the Invention

Compounds are provided that interfere with c-Myc activity along with uses for the compounds and formulations containing the compounds. Also described is a high-throughput method for screening for drugs that interfere with c-Myc activity.

2. Description of the Related Art

Members of the Myc oncoprotein family, which includes c-Myc, N-Myc, and L-Myc, are frequently deregulated in human cancers. In addition to their transforming properties, these proteins may contribute to the neoplastic phenotype by inhibiting differentiation, reducing growth factor requirements, inducing genomic instability, and promoting angiogenesis. Myc proteins are basic helix-loop-helix-leucine zipper (bHLH-ZIP) transcription factors whose known biological activities require that they heterodimerize with the bHLH-ZIP protein Max (B. Lüscher, L-G. Larsson (1999), *Oncogene* 18:2995). Mostly as a result of DNA microarray analyses, a large number of positive and negative transcriptional targets for c-Myc have now been identified. Many of these encode proteins that participate in cell growth and metabolism, apoptosis, and extracellular matrix formation, and a number of these are also transforming in their own right. Such functional redundancy suggests that therapies based on the specific inhibition of individual Myc target gene products may be difficult to attain. Rather, the specific inhibition of c-Myc itself may be a more viable alternative.

Previous attempts to inhibit c-Myc function have utilized approaches such as antisense oligonucleotides or gene transfer of Mad family member proteins, which are HLH-ZIP partners of Max that negatively regulate c-Myc. These approaches have had some limited experimental success, but suffer from both theoretical and practical limitations.

As an example of the role c-Myc plays in many cancers, several independent lines of evidence suggest a role for c-Myc in the causation of prostate cancer. Jenkins et al. (Jenkins, R. B., et al. (1997), *Cancer Res.*, 57:524–31.) used FISH and immunocytochemistry to evaluate the status and expression of c-Myc in 48 matched samples of high-grade prostatic intraepithelial neoplasia (PIN) (48 foci), localized prostatic carcinoma (71 foci), and metastases (23 foci). Large increases in c-Myc copy number relative to the chromosome 8 centromere, and concurrent increases in c-Myc immunoreactivity, were observed in 0%, 8% and 21% of foci of PIN, carcinoma, and metastases, respectively. Significant intratumoral molecular heterogeneity was also observed, suggesting the independent and simultaneous evolution of tumor cells within an otherwise histologically uniform focus. A more recent report using both FISH and comparative genomic hybridization (CGH) has provided confirmation for some of these findings by demonstrating >3-fold amplification of c-Myc in 29% of prostatic carcinomas. Several other studies have found similarly high levels of c-Myc amplification.

Mad bHLH-ZIP family members antagonize Myc function and are thus potential tumor suppressors (Luscher, B. and L. G. Larsson (1999)). Mxi1, one of the members of this family, has been mapped to 10q25, a region that is commonly deleted in prostate cancer (Shapiro, D. N., et al. (1994), *Genomics*, 23:282–5). Evidence is presented for deletion and inactivation of Mxi1 in approximately one-half of primary prostate cancers (Eagle, L. R., et al. (1995), *Nat Genet.*, 9:249–55 and Prochownik, E. V., et al. (1998), *Genes Chromosomes Cancer*, 22:295–304). Subsequent work has shown that Mxi1 −/− mice develop prostatic dysplasia (Schreiber-Agus, N., et al., (1998), *Nature*, 393: 483–7).

SUMMARY

A high throughput method for screening compounds for their affect on Myc function is described. Using this method a number of compounds were identified from a combinatorial chemical library of over 10,000 compounds that interfere specifically with c-Myc function, interfere with cell growth and prevent tumor formation. More specifically, the following are described.

A method for interfering with Myc function, cell growth and/or tumor growth that includes the step of contacting a cell or tumor, or administering to a patient, an amount of an active compound effective to either interfere with Myc function, inhibit cell growth and/or inhibit tumor growth. Tumors or cancers especially susceptible to regulation by the described compounds include prostate cancer, breast cancer, colon cancer and Burkitt's Lymphoma. Compounds useful in these methods include seven parent compounds (a-g):

(a) Bicyclo[2.2.1]hept-2-yl-[2-(4-nitro-phenyl)-ethyl]-amine; (b)1-[2,5-Dioxo-1-(4-propoxy-phenyl)-pyrrolidin-3-yl]-piperidine-4-carboxylic acid; (c) 4-Methyl-2-[N'-(6-methyl-2-phenyl-chroman-4-ylidene)-hydrazino]-thiazole-5-carboxylic acid (3-nitro-phenyl)-amide; (d) 5-(4-Ethyl-benzylidene)-2-thioxo-thiazolidin-4-one; (e) 3-[3-(3,6-Dichloro-carbazol-9-yl)-2-hydroxy-propyl]-thiazolidine-2,4-dione; (f) biphenyl-2-yl-(7-nitro-benzo[1,2,5]oxadiazol-4-yl)-amine; and (g) 1-(3-chloro-phenyl) -3-diethylamino-pyrrolidine-2,5-dione. Also useful in the methods described herein are derivatives and salts of parent compounds (a-g) that interfere with Myc and Max association function and cell and tumor growth as determined by the assays described herein.

The above-described active compounds are demonstrated as useful in inhibiting cell growth and tumor formation. Compositions therefore are provided that facilitate delivery of those active compounds, such as emulsions, including oil in water emulsions and liposomes, and complexes with solubilizing agents, such as cyclodextrins and polyoxyethylene-conjugated vegetable oils. The compositions include an active compound, as described herein, and an excipient.

The described parent compounds (a-g) also are useful as starting points for rational drug development methods, either in silico or by more conventional "wet" chemical synthesis and screening methods. In the in silico methods, computerized processes are used to screen derivatives of the lead compounds for their effect on the association of Myc and Max. Additional derivatives having one or more groups substituted with a different group. Any derivative can be screened according to methods described herein.

BRIEF DESCRIPTION OF THE DRAWINGS

FIGS. 4A–D are graphs showing inhibition of mammalian cell growth in vitro by the seven Myc-Max-specific compounds. FIG. 4A-R*at*1a-neo cells. FIG. 4B-R*at*1a-c-Myc fibroblasts. FIG. 4C-P*arental* TGR-1 cells. FIG. 4D-c-Myc KO cells.

FIG. 7A is compound 10075-G5 and FIGS. 7B–E are the results of in silico screening of compounds of the Chembridge library as described in

DETAILED DESCRIPTION

Figure 1B:
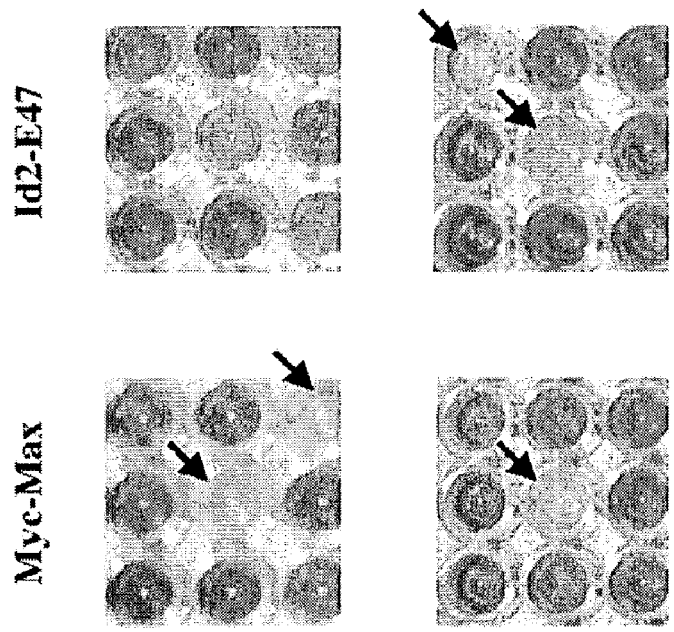
FIG. 1B are photographs of portions of microfilter plates showing examples of the responses in the yeast two-hybrid screening methods described in the Examples.

The use of numerical values in the various ranges specified in this application, unless expressly indicated otherwise, are stated as approximations as though the minimum and maximum values within the stated ranges were both preceded by the word "about." In this manner, slight variations above and below the stated ranges can be used to achieve substantially the same results as values within these ranges. Also, the disclosure of these ranges is intended as a continuous range including every value between the minimum and maximum values.

As described above, a yeast two-hybrid assay was used to screen compounds that potentially affect the interaction between c-Myc and Max. Seven compounds were seen to interfere specifically with that interaction and later were found to affect c-Myc function in vitro and in vivo, and therefore, directly affect cell growth and proliferation. These compounds therefore have significant utility not only as potential anti-cancer therapeutics, but as lead compounds for the identification of second generation analogs of the lead compounds that also would be expected to have potent anti-growth and anti-cancer activity.

Yeast two-hybrid assays are described in C. Bai, S. J. Elledge, *Methods Enzymol.*, 273, 331 (1996) as well as in U.S. Pat. Nos. 5,128,256, 5,283,173, 5,286,636 and 5,468,614. A number of yeast two-hybrid systems also are commercially available, such as the HybriZAP 2.1 Two Hybrid System, commercially available from Stratagene of La Jolla, Calif. and the MATCHMAKER two-hybrid system, commercially available from BD Biosciences Clontech of Palo Alto, Calif.). In the present case, the HLH-ZIP domains of c-Myc and Max were fused to the DNA binding domain (BD) and transcriptional activation domain (AD), respectively, of the yeast GAL4 transcription factor. The association between c-Myc-BD (the "target") and Max-AD (the "bait") results in the de facto reconstitution of a fully functional transcriptional activator. A β-galactosidase gene, containing a GAL4 binding site in its promoter, and residing within the yeast genome, is highly induced upon the binding of c-Myc-Max, thus providing a simple, rapid, and quantitative readout of the proteins' dimerization state. Compounds that disrupt the association of the target and the bait would therefore prevent induction of the enzyme. To control for non-specific effects, a second yeast strain was created in which BD and AD fusions with the HLH proteins Id2 and E47, respectively, were expressed.

Each of the yeast strains (referred to as Myc-Max and Id2-E47) was used to screen a chemical library of approximately 10,000 low molecular weight compounds. Seven compounds were identified that markedly inhibited β-galactosidase activity in Myc-Max yeast but not in Id2-E47 yeast. Similarly, 10 compounds were identified that selectively inhibited enzyme activity in Id2-E47 yeast but not in Myc-Max yeast, and 28 compounds were identified that inhibited enzyme activity in both yeast strains ("dual-specific").

Rat1a-c-Myc cells form rapidly growing tumors in nude mice. Four of the Myc-Max-specific compounds were analyzed to determine if they also could inhibit in vivo tumor growth. All four compounds significantly reduced tumor growth in comparison to that seen following inoculation with Rat1a-c-Myc cells exposed to the DMSO vehicle only.

The results presented here indicate the feasibility of utilizing the yeast two hybrid system to identify low molecular inhibitors of c-Myc, an HLH-ZIP protein with strong oncogenic potential that is frequently deregulated in human cancers. Because the frequency with which these compounds also inhibit c-Myc function in mammalian cells is quite high, yeast-based approaches may be of more general utility in identifying potential chemotherapeutic agents.

All of the compounds identified appear to act directly by preventing or markedly de-stabilizing the c-Myc-Max association. While it might initially seem surprising that such simple molecules could affect protein-protein associations that occur over relatively large interfaces, it should be recalled that single amino acid substitutions in HLH and ZIP domains of c-Myc and other proteins have long been known to prevent such associations, to alter their DNA binding specificity, and to inhibit their biological function (R. Turner R Tjian, (1989) *Science* 243:1689; M. J. Smith, D. C. Charron-Prochownik, E. V. Prochownik, (1990), *Mol. Cell. Biol.*, 10:5333; M. E. Van Antwerp, D. G. Chen, C. Chang, E. V. Prochownik, (1992), *Proc. Natl. Acad. Sci. USA;* 89:9010; and E. Bengal, et al., (1994), *Proc. Natl. Acad. Sci. USA*, 91:6221). More recently, low molecular weight compounds have been identified that prevent interactions between members of the Bcl-2 oncoprotein family, that inhibit selective p53 functions such as transcriptional activation and apoptosis, and that promote the reversion of p53 from a mutant to a wild-type conformation (P. G. Komarov et al., (1999), *Science* 285:1733–1737; J. L. Wang, D. Liu, Z. J. Zhang et al., (2000), *Proc. Natl. Acad. Sci. USA*, 97:7124–7129; and B. A. Foster, H. A. Coffey, M. J. Morin, F. Rastinejad, (1999) *Science* 286:2507–2510). That each of the molecules identified in the screenings of the examples, below, shows a signature inhibitory profile for the various HLH and HLH-ZIP interactions tested (FIG. 2) further suggests that they may interact with different regions of these domains. This indicates that enhanced anti-tumor efficacy might be achieved with combinations of these compounds. Finally, the approaches reported here provide a means by which structural analogs based upon the parent, lead, or first generation Myc-Max inhibitors can be evaluated readily for various desirable properties. The recent report that transient reductions in c-Myc can produce in vivo tumor regression (Jain M, Arvanitis C, Chu K, Dewey W, Leonhardt E, Trinh M, Sundberg C. D., Bishop J. M., Felsher D. W. (2002), *Science,* 297:102–104) is consistent with the data presented here (FIG. 4), and supports the idea that even short-term pharmacologic inhibition of Myc oncoproteins is an attractive therapeutic strategy.

Berg et al. (Berg T, Cohen S B, Desharnais J, Sonderegger C, Maslyar D J, Goldberg J, Boger D L and Vogt P K, (2002), *Proc. Natl. Acad. Sci. USA,* 99:3830–3835) reported results similar to those presented herein. In that reference, the screening assay, however, utilized an in vitro-based system in which loss of fluorescence resonance energy transfer between green fluorescent protein-tagged c-Myc and Max was used as a way of assessing the ability of small molecules to disrupt the heterodimer. The compounds identified by Berg et al. also were effective in the low micromolar range. However, differences in the biological activities of some of those compounds were seen in that they did not inhibit colony formation by transformed cells expressing endogenous levels of c-Myc. That study provides further independent support for the idea that low-molecular-weight compounds can inhibit protein-protein interactions that normally occur over relatively large surfaces.

Figure 1A:
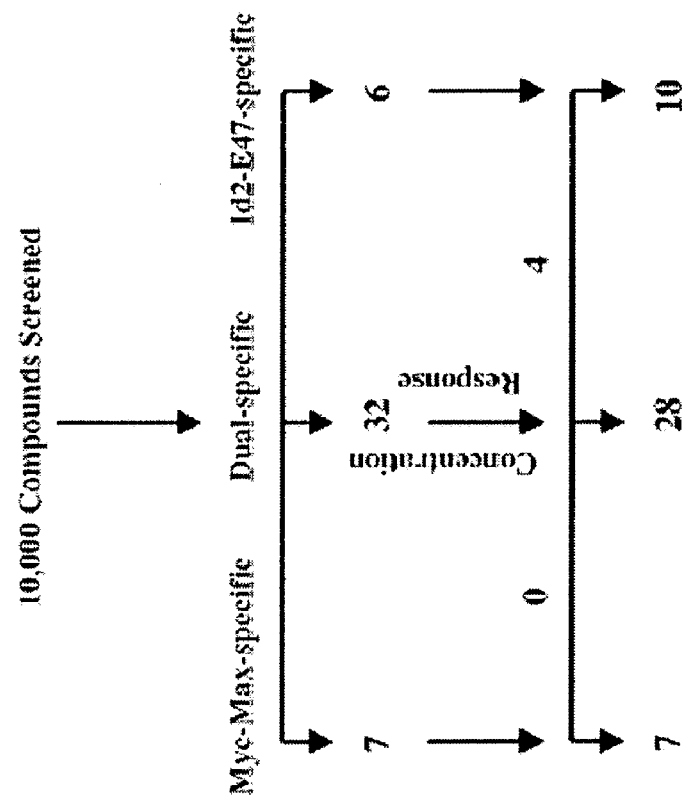
FIG. 1A is a flowchart that outlines the results of a high throughput screening method performed as described in the Examples.
Figure 2:
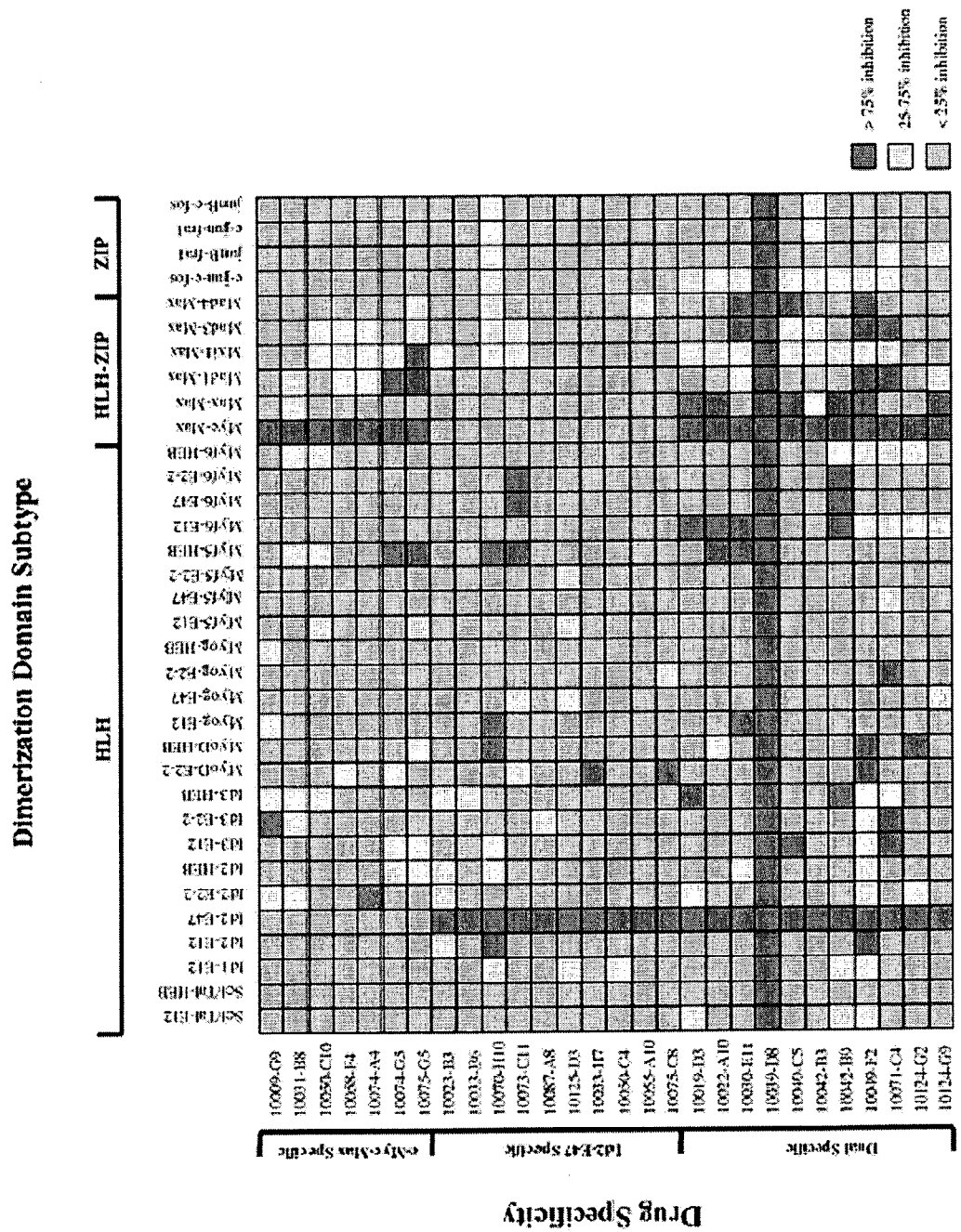
FIG. 2 is a matrix showing a multiplex analysis of inhibitory specificities of the compounds identified as c-Myc-Max-specific, Id2-E47-specific or dual-specific.

Finally, it should be noted that secondary outcome of the study described herein was the identification of compounds that are quite specific for the Id2-E47 heterodimer (FIGS. 1 and 2). Id proteins serve as negative regulators of a variety of tissue-specific differentiation processes, may promote proliferation by virtue of their interaction with specific cell cycle regulators, and are overexpressed in some cancers (Hasskarl J. and Munger K. (2002), Cancer Biol. Ther., 1:91–96). This suggests that the molecules described herein as interfering specifically with the Id2-E47 heterodimer (see, for example, the matrix of FIG. 2), might be employed as an antiproliferative active agent or in combination with compounds that interfere with Myc-Max association in certain cancer therapies.

Structural analogs of the lead compounds described herein generally are identical to the first generation compounds except that they have one or more groups replaced with different groups, whether the groups are monovalent or multivalent (having two or more bonds). Groups typically are replaced by physically or chemically similar groups as is common in the art, such as, without limitation, the replacement of halides for other halides, $C_{1-6}$ (lower) alkane groups for other lower alkane groups, methyl for H, alkylcarboxyl for carboxyl, and one salt form for another. The analogs, by virtue of the different groups may exhibit improved specific activity, solubility, stability, half life and bioavailability as compared to the first generation compounds. Examples of groups that may be replaced, and candidate substitute groups include, without limitation: H; halogen; alkyl (straight, cyclic or branched chain); alkenyl (straight, cyclic or branched chain); alkynyl (straight, cyclic or branched chain); halo-alkyl, -alkenyl or -alkynyl; CN; $CF_3$; aryl (for instance, and without limitation, phenyl, benzyl, naphthyl groups and including substituted aryl groups in which any or all H groups of the aryl ring is substituted with a group, as defined herein); heterocycl (for instance and without limitation, pyridyl, furyl, pyrrolyl, thienyl, imidazolyl, pyrazolyl, pyrimidinyl and purinyl groups, including N—, O—and S—substituted heterocycyls and also including substituted heterocycl groups in which any or all groups of the aryl ring is substituted with a group, as defined herein); carboxyl; carbonyl, alkoxyl; alkyloxyalkanes; alkoxycarbonyl; aryloxyl, heterocyclyloxyl; hydroxyl; amine; amide; amino; quaternary amino; nitro; sulfonyl; alkylamine; silyl, siloxyl; saturated C—C (carbon-carbon) bonds; unsaturated C—C bonds; ester, ether, amino; amide, urethane, carbonyl, acetyl and ketyl groups; hetero atoms, including N, S and O; polymer groups (such as, without limitation hydrophilic or hydrophobic groups, and including, without limitation, polyoxyethylene and peptides); and amino acid groups.

Figure 7A:
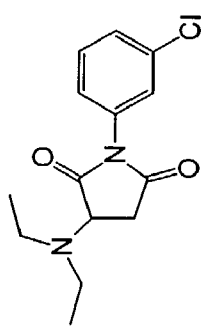
Figure 7C:
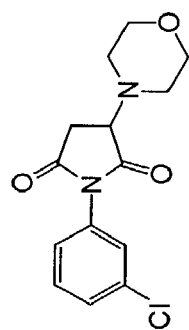
Figure 7E:
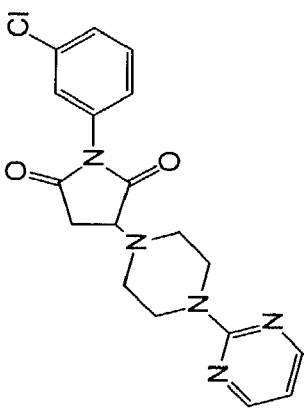
Figure 7B:
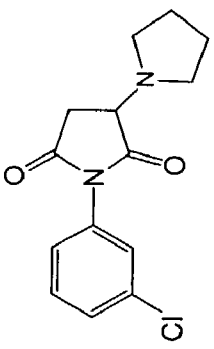
Figure 7D:
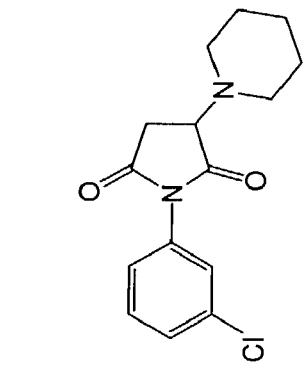

An example of a parent compound and structural analogs of that compound is provided in FIGS. 7A–E. FIG. 7A provides the structure of the lead compound 10075-G5. FIGS. 7B–7E provide structures of structural analogs of 10075-G5. Thus, one species of the active agents provided herein is the compound:

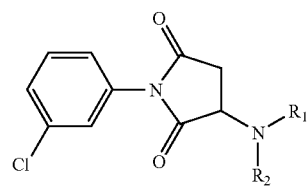

wherein $R_1$ and $R_2$ are lower alkyl or are combined to form a saturated or unsaturated heterocyclic $C_{4-10}$ ring, for example a heterocyclic $C_{5-6}$ ring, optionally with one or more additional carbons of the ring replaced with an O, N or S and wherein the heterocyclic ring is optionally substituted with one or more monovalent groups as described above, for example with a pyrimidyl group as shown in FIG. 7E.

The structural analogs or derivatives can be analyzed for their interference with c-Myc/Max association by the aforementioned two-hybrid assay, or by any method for determining anti-cancer activity of a compound. For instance, the activity of the analog can be determined by screening using the yeast two-hybrid based approach mentioned above, followed by testing the positive compounds for their affect on cultured tumor cells and/or in vivo, as described herein. The yeast two-hybrid based approach is a high-throughput method, but does not necessarily have to be used to screen each derivative. The derivatives may be screened more directly by determining their effect on the growth of plated cells.

The results presented herein demonstrate the utility of the yeast two-hybrid system for identifying selective low molecular weight inhibitors of c-Myc, a bHLH-ZIP oncoprotein that is often deregulated in human cancer. Since the frequency with which these compounds inhibit c-Myc function in mammalian cells is quite high, yeast-based approaches may be of more general utility in predicting potentially useful chemotherapeutic agents.

The compounds described herein have significant therapeutic potential due to the well-established, direct role c-Myc plays in the etiology of many cancers, such as prostate cancer, breast cancer, colon cancer and Burkift's Lymphoma.

For example, a variety of studies indicate that c-Myc plays an essential role in the pathogenesis, evolution, or survival of prostate cancer, and that disruption of the Myc/Max network would provide effective therapy not only for prostate cancer but for many other cancer types as well. This evidence derives from five different types of studies.

First, c-Myc is amplified and/or over-expressed in primary and metastatic tumors. Numerous investigators have demonstrated amplification of c-Myc in prostate cancer and in some cases have documented a correlation between the degree of amplification and tumor stage or survival (Nesbit, C. E. et al. (1999), *Oncogene,* 18:3004–16 and www.myc-cancer-gene.org/site/cancerDB.asp for a comprehensive listing of the association of c-Myc oncoproteins and Human tumors).

Second, loss of tumor suppressors that regulate c-Myc function are identified in many prostate cancers. Mxi1 negative regulator of the c-Myc pathway, is deleted in approximately 50% of prostate cancers. In some cases, this is associated with mutational inactivation of the non-deleted allele (Prochownik, E. V., et al. (1998), and Eagle, L. R., et al. (1995), *Nature Genet.,* 9:249–55). Bin1, a protein that interacts with and exerts a negative regulatory effect on c-Myc, also is inactivated or deleted in a significant fraction of prostate cancers (Duhadaway et al. (2003) *J. Cell Biochem.,*88:635–642 and Ge K. et al. (2000), *Int. J. Cancer,* 86:155–161).

Third, animal models indicate the influential role of c-Myc in prostate cancers. Transgenic mice with prostate-specific expression of c-Myc, alone, develop dysplatic lesions, which resemble those of low-grade PIN, but which do not progress to actual adenocarcinomas (Zhang X. et al. (2000) *Prostate,* 43:278–285). In contrast, the transgenic co-expression of c-Myc and ras, with or without concurrent loss/inactivation of p53, leads to the development of frank malignancy (Greene D. R. et al. (1995) *Int J. Cancer,* 60:395–399, Nupponen N. N. et al. (1998) *Am. J. Pathol.* 153:141–148 and Jenkins, R. B., et al. (1997), *Cancer Res.,* 57:524–31). A knockout of mxi1 also was shown to lead to prostatic dysplasia as well as to cooperate with other oncogenic lesions (Schreiber-Agus, N. et al. (1998), *Nature,* 393:483–7).

Fourth, anti-sense-mediated suppression of c-Myc or over-expression of Mxi1 has been shown to result in anti-proliferative effects in a number of prostate cancer models (Taj M. M. et al. (2001), Prostate 47:194–204 and Steiner et al. (1998), *Human Gene Ther.,* 9:747–55).

Lastly, c-Myc plays a significant role in cell cycle progression, survival, and transformation by other oncogenes. It is known for nearly a decade that the c-Myc knockout animal is an embryonic lethal, and that primary fibroblasts from such animals cannot be established in vitro (Davis A. C. et al. (1993) *Genes Dev.* 7:671–682). More recent evidence has also shown that conditional inactivation of c-Myc in primary cells leads to an abrupt cessation of growth and eventual apoptosis (deAlboran, et al. (2001), *Immunity* 14:45) and that even a 50% reduction of c-Myc levels in fibroblasts inhibits their transformation by other oncogenes by >90% without affecting proliferation (Bazarov A. V. et al. (2001) *Cancer Res.* 61:1178–1186). Therefore, even if c-Myc were not directly responsible for the generation of a malignancy, its targeting is expected to significantly affect cell proliferation.

In summary, there exists strong evidence to support the notion that c-Myc and members of its network play important roles in the initiation and/or evolution of prostate cancer. In addition, the unequivocal involvement of c-Myc in many other human cancers (especially breast, colon, and lymphoid malignancies), and its central role in cellular proliferation makes it a particularly attractive target, even if abnormal expression of c-Myc is not the sole "cause" of the cancer. Estimates of c-Myc involvement in human cancers based solely on its amplification or over-expression may underestimate the true contribution made by this oncoprotein. Rather, its relative functional level appears to be a more accurate determinant of its neoplastic potential.

The compounds described herein may be administered by any effective route. Typical administration routes for anti-cancer drugs include, without limitation, oral and parenteral routes, such as intravenous (IV) injection. The compounds described herein are useful in interfering with c-Myc and Max association. In any case, the drug should be administered in amounts effective to cause a desired anti-cancer effect, typically in the range of from about 0.001 μM to about 50 μM, preferably from about 0.01 μM to about 50 μM. Because the compounds have, in some cases, limited solubility in aqueous solutions, one or more methods for increasing the solubility of the drugs, such as the use of emulsions, such as oil-in-water-emulsions; liposomes and solubility-enhancing compositions, such as a vegetable oil that is conjugated with (attached to) a solubilizing group such as polyethylene glycol or like compounds, for example, Cremophore EL (polyoxyethylene-conjugated castor oil) and α-, β- and γ-cyclodextrins and partially or completely substituted versions thereof, such as, without limitation, hydroxypropyl-β-cyclodextrin or sulfobutyl ether-7-β-cyclodextrin and other cyclodextrin ethers (see, U.S. Pat. Nos. 5,472,954, 6,046,177 and 6,407,079 for examples of cyclodextrin-drug complexation methods and related formulations). As used herein, "excipients" are compounds or compositions that, along with the active ingredient, are included in a formulation. Examples of excipients include, without limitation, carriers, solvents, emulsifiers, solubilizing agents, colorings, flavorings, sweeteners, lubricants, matrices and fillers. A typical dosage form would contain an amount of a compound effective to inhibit cell growth to a desired extent and a pharmaceutically acceptable excipient or excipients. This amount would naturally vary depending on the specific activity of the compound, the delivery route and the choice of solubilizing agents, among other factors. For example, a dosage form might include about 1 μg per kg of a patient's body weight to about 1 mg per kg of the patient's body weight of the compound, effective ranges might be narrower to range from about 100 μg per kg of patient body weight to about 1 mg per kg of patient body weight.

EXAMPLES

Materials and Methods

A. Yeast Two-Hybrid Assays

Fusions between the Gal4 DNA-binding domain (BD) of c-Myc and Id2 in the pGBT9 vector have been previously described, as have fusions between the Gal4 activation domain (AD) and Max and E47 in the pGAD vector (Langlands K, Anand G, Yin X and Prochownik E. V., (1997), *J. Biol. Chem.,* 272: 19785–19793). The construction and characterization of other BD and AD fusion partners have also been previously described (Langlands et al., 1997;

Grove L, Datta N, Long M W and Prochownik E. V., (1999a), *Oncogene*, 17;1177–1184). Each included at least the minimal HLH, ZIP, or HLH-ZIP domain that had been amplified from various parental vectors using the polymerase chain reaction. All primers were prepared with EcoRI and BamHI or BglII restriction sites to allow for directional cloning of the products into the pGBT9 BD or pGAD424 AD vectors. Each individual plasmid was first tested to ensure that it did not self-transactivate the β-galactosidase reporter when expressed in the Y153 yeast strain (not shown). To perform quantitative assays, each yeast strain was grown overnight at 30° C. standard SC medium lacking leucine and tryptophan. The cultures were diluted in the same medium to an $OD_{600}$ of 0.15 and 50 ml were inoculated into 96-well plates using a Biomek2000 Laboratory Automated Workstation (Beckman-Coulter, Brea, Calif., USA) just prior to the addition of compounds.

B. Low-Molecular-Weight Compound Library Screening

The DIVERSet combinatorial library (Chembridge, Inc., San Diego, Calif., USA) includes 10,000 drug-like small molecules (average molecular weight=350 Da), which were selected based on 3D pharmacophore analysis to cover the broadest part of biologically relevant pharmacophore diversity space. Each compound was dissolved in DMSO at an average concentration of 14 mM. A stock solution (0.5 µl) of each compound was added to triplicate wells of yeast and incubated at 30° C. with constant agitation for approximately 18 h until the yeast had reached saturation densities. The average final concentration of each compound was 10 µM. The $OD_{600}$ of each well was determined on a SpectraMax Plus automated plate reader (Molecular Devices, Sunnyvale, Calif., USA) and compared to the ODs of control wells that had been inoculated with DMSO only. Under these conditions, DMSO had no effect on the growth of yeast and none of the compounds inhibited growth by >50%. β-galactosidase assays were then performed overnight as previously described (Langlands et al., 1997; Yin XY et al., (1999a)) using chlorophenol red-β-d-galactopyranoside (CPRG) (Roche Applied Science, Mannheim, Germany) as a substrate. ODs were determined at 580 nm, again using the automated plate reader. After normalizing for differences in densities of the yeast, the degree of β-galactosidase inhibition was ranked as minimal (<25%), moderate (25–75%), or marked (>75%). Each determination was performed in triplicate and all compounds identified as giving marked inhibition were confirmed on multiple subsequent occasions. Compounds registering as positive were re-assayed in triplicate in order to determine $IC_{50}$'s, and errors were generally <5%. Chemical identities for each of the Myc- Max-specific compounds were: #10009-G9: bicyclo[2.2.1]hept-2-yl-[2-(4-nitro-phenyl)-ethyl]-amine; #10031-B8: 1-[2,5-dioxo-1-(4-propoxy-phenyl)-pyrrolidin -3-yl]-piperidine-4-carboxylic acid; #10050-C10: 4-methyl-2-[N'-(6-methyl-2-phenyl-chroman-4-ylidene)-hydrazino]-thiazole-5-carboxylic acid (3-nitrophenyl)-amide; #10058-F4: 5-(4-ethyl-benzylidene)-2-thioxothiazolidin-4-one; #10074-A4: 3-[3-(3,6-dichloro-carbazol-9-yl)-2-hydroxy-propyl]-thiazolidine-2,4 -dione; #10074-G5: biphenyl-2-yl-(7-nitro-benzo[1,2,5]oxadiazol-4-yl)-amine; #10075-G5: 1-(3-Chloro-phenyl)-3-diethylamino-pyrrolidine-2,5-dione.

C. GST Pull-Down Experiments

A human c-Myc cDNA in the pBluescript SK+ vector (Stratagene, La Jolla, Calif., USA), was transcribed and translated in vitro with T7 RNA polymerase using the TnT expression system (Promega, Madison, Wis., USA) according to the directions of the supplier. The reaction was performed in the presence 20 µCi of [$^{35}$S]methionine (Perkin-Elmer, Boston, Mass., USA, specific activity 1175 Ci/mmol) at 32° C. for 90 min. One tenth of the reaction was mixed on ice with 500 ng of recombinant, affinity-purified GST-Max protein in a total volume of 50 ml of dilution buffer (10% glycerol, 100 mM KCl; 10 mM Tris-HCl; 1 mM EDTA; 1 mM dithiothreitol) (Yin et al., (1999a)). In all, 1 µl of each compound, dissolved as a stock solution in DMSO, was then added to give a final compound concentrations ranging from 5 to 50 µM. The complete reactions were incubated for 30 min at 40° C. to allow for dimerization between the two proteins. At the end of the incubation, 1 µl of binding buffer and 50 µl of washed glutathione-agarose beads (BioRad, Hercules, Calif., USA) were added for 5 min with constant agitation. The beads were then pelleted by centrifugation, washed three times in binding buffer, and resuspended and boiled for 5 min in SDS-PAGE running buffer. The sample was resolved by SDS-PAGE on a 10% polyacrylamide gel, which was then dried and autoradiographed.

D. Mammalian Cell Culture and Transfections

Rat1a-neo, Rat1a-c-Myc, Rat1a-MycER, and C3H10T1/2 cells have been previously described (Van Antwerp, et al., 1992; Yin et al., (1999a); and Yin X. Y., Gupta K., Han W. P., Levitan E. S. and Prochownik E. V. (1999b), *Oncogene*, 18:6621–6634). TGR-1 fibroblasts and the derivative c-Myc 'knockout' (KO) cell line HO15.19 were also as described (Matayek M. K., Obaya A. J., Adachi S. and Sedivy J. M. (1997), *Cell Growth Differ.*, 8:1039–1048; Yin et al. (1999b)). All cells were cultured in Dulbecco's modified minimal essential medium (D-MEM) supplemented with 10% fetal calf serum, 2 mm glutamine, and penicillin and streptomycin (all from Gibco-BRL, Grand Island, N.Y., USA). Rat1a-MycER and HO15.19 cells were also routinely maintained in 1 µg/ml puromycin (Sigma) and 200 mg/ml G-418 (Gibco-BRL), respectively. Transient transfections of the pSVL-c-Myc and pSVL-Max expression vectors (each at 2 µg/plate) and the 3XMyc-adenoE1b-luciferase reporter vector (1 µg/plate) in C3H10T1/2 cells were performed in 60 mm tissue culture plates as described (Zhang H., Fan S. and Prochownik E. V. (1997), *J. Biol. Chem.*, 272:17416–17424). Transient transfections of pRcCMV-MyoD and pRcCMV-E12 (each at 2 µg/plate), and the p3300MCK-CAT reporter vector (1 µg/plate) in the same cells were also performed as described (Van Antwerp et al., 1992). All transfections also contained 1 µg/plate to pCMV-β-galactosidase to control for transfection efficiencies). In all cases, luciferase and CAT assays were performed as previously described (Van Antwerp et al., (1992) and Zhang et al., (1997)) after normalizing for differences in β-galactosidase levels.

E. Ornithine Decarboxylase and Cell Cycle Assays

This assay was performed as previously described (Nesbit C. E., Grove L. E., Yin X. Y. and Prochownik E. V. (1998), *Cell Growth Differ.*, 9:731–741; Nesbit C. E., Tersak J. M., Grove L. E., Drzal A., Choi H. and Prochownik E. V. (2000), *Oncogene*, 19:3200–3212; and Yin X. Y., Grove L., Datta N., Katula K., Long M. W. and Prochownik E. V. (2001), *Cancer Res.*, 61:6487–6493). Cell cycle profiles were performed on propidium iodide-stained nuclei as previously described (Yin et al., (1999a)) using a Becton-Dickinson FACStar flow cytometer. A total of $2\times10^4$ cells were analyzed in triplicate for each point and quantitation was performed using single histogram statistics.

F. Cell Growth and Tumorigenicity Assays

Figures 4A, 4B:
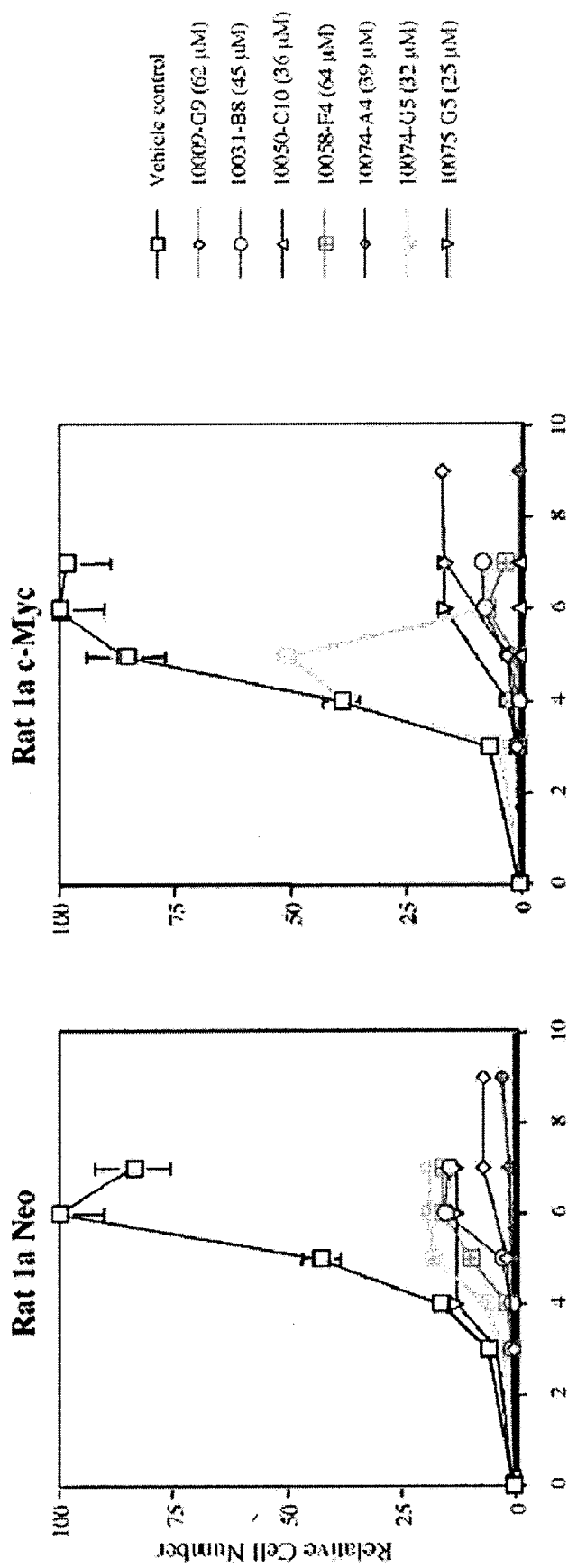

All growth curves were performed in 12-well tissue culture plates as previously described (Yin et al., (1999b)). Rat1a-neo, Rat1a-c-Myc, and TGR-1 fibroblasts were seeded at an initial density of $2 \times 10^3$ cells/well whereas HO15.19 c-Myc KO cells were seeded at $5 \times 10^3$ cells/well. The following day, each compound, or DMSO vehicle alone, was added to the indicated final concentrations. Fresh medium and compound were added every 3–4 days. Cells were trypsinized and manually counted at the indicated times. In all of the above cases, TUNEL assays performed 4–5 days after the addition of the compounds showed that fewer than 15% of the cells were undergoing apoptosis (not shown). For in vivo assays, Rat1a-c-Myc cells were grown to approximately 50% confluency. Fresh medium plus the indicated compounds, or DMSO vehicle alone, were then added to cells for an additional 3 days. The final concentration of each compound was as indicated in FIGS. 4A and 4B. At the end of this time, none of the cultures contained fewer than 10% apoptotic cells as determined by trypan blue staining and TUNEL assays. The cells were then washed twice in PBS, trypsinized and resuspended in a minimal volume of fresh medium containing the same concentration of compound. In total, $2 \times 10^7$ cells were then inoculated subcutaneously into the flanks of nude mice (five animals per group) and no additional compound was administered for the duration of the experiment. Tumor growth was monitored weekly and the average tumor volume (71 s.e.) was calculated as previously described (Yin X. Y., Grove E., Rogulski K. and Prochownik E. V., (2002), *J. Biol. Chem.,* 277:19998–20010).

Example 1

Identification of c-Myc-Max-Specific Compounds by Yeast Two-Hybrid Screening

A yeast two-hybrid-based approach (Bai C and Elledge S J, (1996), *Methods Enzymol.,* 273: 331–347) in which the HLH-ZIP domains of c-Myc and Max were fused to the DNA-binding domain (BD) and transcriptional activation domain (AD), respectively, of the yeast Gal4 transcription factor (Langlands K, et al. 1997; Yin X Y, et al., 1999a). The association between c-Myc and Max results in the de facto reconstitution of a fully functional transcriptional activator. A β-galactosidase gene containing a Gal4-binding site in its promoter and residing within the yeast genome, is induced upon the binding of c-Myc-Max, thus providing a simple, rapid, and quantitative readout of the proteins' dimerization status. Compounds that disrupt this association should therefore prevent induction of the enzyme. To control for nonspecific effects, a second yeast strain was created in which BD and AD fusions with the HLH proteins Id2 and E47, respectively, were expressed. It has been shown previously that the interaction between these proteins can also be accurately and quantitatively assessed (Langlands et al., 1997).

Each of the above yeast strains (hereafter referred to as Myc-Max and Id2-E47) was used to screen a chemical library of 10 000 low-molecular-weight compounds. Seven were identified that markedly inhibited β-galactosidase activity in Myc-Max yeast but not in Id2-E47 yeast (FIG. 1A). Similarly, 10 compounds were identified that selectively inhibited enzyme activity in Id2-E47 yeast but not in Myc-Max yeast, and 28 "dual specific" compounds were identified that inhibited enzyme activity in both yeast strains. A determination of $IC_{50}$'s for all Myc-Max and Id2-E47 compounds, each performed in triplicate, indicated a range of 0.8–7 µM.

FIG. 1A is a flowchart showing identification of Myc-Max and Id2-E47 inhibitors. Myc-Max and Id2-E47 yeast were grown in the presence of each compound for approximately 18 h before performing β-galactosidase assays. Compounds inhibiting enzyme activity >75% compared to controls are indicated. Dual-specific compounds were then retested at 2–4-fold lower concentrations to uncover any previously unrecognized specificities. Under these conditions, four additional compounds, all selective for Id2-E47, were identified. Further evaluation of all the Myc-Max and Id2-E47 compounds, each performed in triplicate, indicated $IC_{50}$'s in the range of 0.8–7 µM. FIG. 1B provides examples of selective β-galactosidase inhibition by Myc- Max-specific, Id2-E47-specific, and dual-specific compounds. Myc-Max and Id2-E47 yeast were grown in the presence of various low-molecular-weight compounds. In the upper set of panels, arrows indicate two compounds that inhibited enzyme activity only in Myc-Max yeast. In the lower set of panels, the arrow in the upper right indicates a compound that selectively inhibited enzyme activity in the Id2-E47 yeast, whereas the center arrow indicates a dual-specific compound. Note that active β-galactosidase registers as a reddish-brown color using the CNPG substrate, whereas its inhibition produces a yellow color.

Example 2

Specificity of Myc-Max Compounds and Their Effects on Myc-Max Heterodimers

To assess further the inhibitory profiles of the above compounds, 32 additional yeast strains were created that express various interacting pairs of HLH-, ZIP-, or HLH-ZIP-containing proteins fused to the above Gal4 domains. Construction of these yeast strains is described in Langlands et al., 1997 and Yin et a., 1999a. This multiplex system was then used to test each of the Myc-Max- and Id2-E47-specific compounds, and 11 of the dual-specific compounds for their abilities to inhibit β-galactosidase activity in each strain. As seen in FIG. 2, both the Myc-Max and Id2-E47 compounds demonstrated remarkable specificities for their originally identified targets. Thus, of the 231 possible combinations of Myc-Max-specific compounds with yeast expressing other protein pairs, only seven (3%) produced marked β-galactosidase inhibition, and of these, three involved the interaction between Max and a Mad family protein member. A similar degree of specificity was seen with the Id2-E47-specific compounds where, of the 330 other possible yeast compound combinations, only nine (2.7%), resulted in a comparable degree of enzyme inhibition. As expected of the dual-specific compounds, somewhat greater promiscuity was observed, with 34 of the 320 possible combinations (10.6%) producing marked β-galactosidase inhibition. However, these too were biased towards interactions involving other members of the Myc network. This analysis excluded compound 10039-D8, which inhibited β-galactosidase activity in every yeast strain tested and likely represents a nonspecific effect due, for example, to inhibition of DNA binding, Gal4-transcriptional activation, or β-galactosidase itself.

FIG. 2 is a matrix showing the multiplex analysis of inhibitory specificities. Yeast strains expressing the indicated combinations of BD and AD fusion proteins were grown as described in Langlands et al., 1997 and Yin et al., 1999a. Each compound was added at the concentration originally used to identify its specificity. β-galactosidase assays were performed at least three times. The degree of enzyme inhibition achieved with each compound is indicated by the relative shade of gray: dark gray: >75% inhibition; light gray: 25–75% inhibition; medium gray: <25% inhibition. In addition to the above, these data suggest that each of compounds demonstrate a unique pattern of heterodimer inhibition. This suggests that each compound might disrupt the Myc-Max HLH-ZIP dimer by interacting with different regions of the dimerization domain. In turn, this suggests that the compounds might show additive or synergistic in vivo effects.

Figure 3:
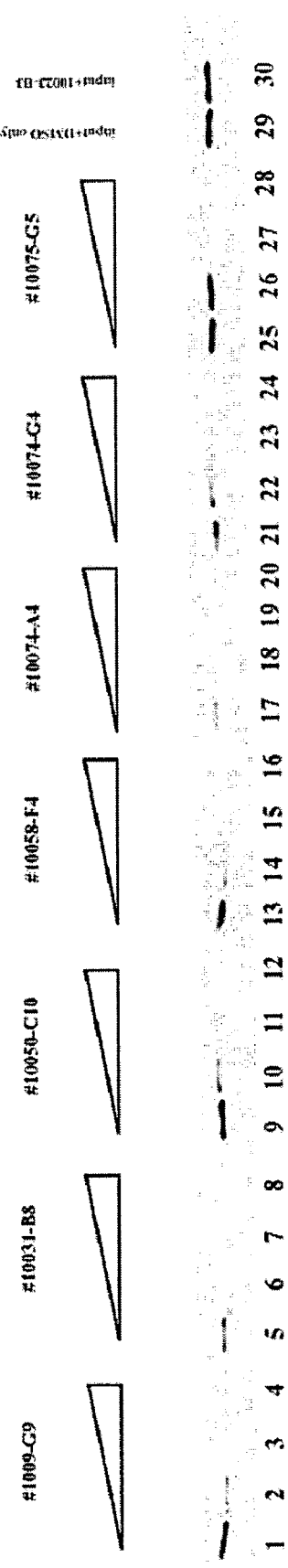
FIG. 3 is an autoradiograph showing direct inhibition of Myc-Max heterodimer formation by the seven Myc-Max-specific compounds.

To determine whether the Myc-Max-specific compounds were acting directly on the heterodimer, c-Myc was expressed as an $^{35}$S-labeled in vitro translated protein (E. V. Prochownik, M. E. VanAntwerp (1993), *Proc. Nat. Acad. Sci. USA,* 90:960). It was then determined whether any of the Myc-Max-specific compounds could prevent its association with a recombinant glutathione-S-transferase (GST)-Max fusion protein. As shown in FIG. 3, each of the seven Myc-Max-specific drugs inhibited this association. No inhibition was seen with any of several Id2-E47-specific compounds or with compounds that failed to inhibit enzyme activity in any of the yeast strains (FIG. 3 and unpublished observations).

FIG. 3 shows the direct inhibition of heterodimer formation by Myc-Max-specific compounds. $^{35}$S-labeled, in vitro translated c-Myc protein was incubated with GST-Max plus 1 µl of the indicated compounds dissolved in DMSO. Compound concentrations were 50, 20, 10, and 5 µM. GST-Max was then precipitated by the addition of glutathione-agarose beads. The captured $^{35}$S-labeled c-Myc protein was released by boiling and resolved by SDS-PAGE. In lane 29, the proteins were incubated with DMSO vehicle only; in lane 30, the proteins were incubated in the presence of 50 µM of the Id2-E47-specific compound 10023-B3.

Example 3

Inhibition of Mammalian Cell Growth by Myc-Max Specific Compounds

Since c-Myc is necessary for the proliferation of mammalian cells (Prochownik, E. V., J. Kukowska, and C. Rodgers (1988), *Mol. Cell. Biol.,* 8:3683–95; I. M. deAlboran, et al. 2001), it was next determined whether the Myc-Max-specific compounds could inhibit this process. Control Rat1a fibroblasts (Rat1a-neo cells) or Rat1a cells transfected with a c-Myc expression vector (Rat1a-c-Myc cells; Yin et al., 1999b) were grown in the presence of each compound and viable cell counts were performed periodically thereafter. As seen in FIGS. 4A and 4B, all of the compounds strongly inhibited the growth of each cell line. During the initial 5–6 days, this was not accompanied by apoptotic cell death, with >90% of the cells remaining viable as determined by trypan blue staining and TUNEL assays (not shown). Longer periods of incubation, however, were accompanied by significant apoptosis in each case. These results are consistent with the idea that the compounds could inhibit c-Myc-Max interactions in mammalian cells even when c-Myc was deregulated and expressed at abnormally high levels. They are also consistent with previous findings that prolonged inhibition of c-Myc in some cases also leads to eventual apoptotic cell death (Kimura S, Maekawa T, Hirakawa K, Murakami A and Abe T. (1995). Cancer Res., 55,1379–1384; Van Waardenburg R C, Meijer C, Burger H, Nooter K, De Vries E G, Mulder N H and De Jong S (1997), *Int. J. Cancer,* 73:544–550.; Ebinuma H, Saito H, Kosuga M, Wakabayashi K, Saito Y, Takagi T, Nakamoto N, Okuyama T and Ishii H (2001), *J. Cell. Physiol.,* 188: 56–66).

As the proliferation of both Rat1a and Rat1a-c-Myc cells was inhibited by the compounds, it was not possible to ascribe this exclusively to the inhibition of c-Myc function. The above experiments were therefore repeated in a rat fibroblast cell line (TGR1) in which the c-Myc gene had been inactivated by homologous recombination (Matayek et al., 1997). As seen in FIGS. 4C and 4D, each compound inhibited the growth of the parental cell line but had little or no effect on the growth of Myc –/– cells. Longer periods of incubation, performed so as to take into account the slower proliferative rate of these cells (Matayek et al., 1997), still failed to result in any significant inhibition of growth rate (not shown).

FIGS. 4A–D show the inhibition of mammalian cell growth by Myc-Max-specific compounds. In FIGS. 4A and 4B, respectively, Rat1a-neo and Rat1a-c-Myc fibroblasts were grown in the indicated concentrations of each compound. Total viable cell counts were then performed at the indicated times. Each point represents the average of triplicate determinations ±1 s.e. FIGS. 4C and 4D show results with Parental TGR-1 cells or c-Myc KO cells, respectively (Matayek et al., 1997) were grown in the indicated concentrations of the Myc-Max-specific compounds or DMSO alone. Cell counts were performed at the indicated times.

It should be noted that none of the compounds affected the growth of c-Myc nullizygous cells, indicating the lack of cytotoxicity of the compounds. These compounds also do not adversely affect the survival of normal quiescent cells maintained in low serum, a condition that normally downregulates c-Myc expression. These experiments suggest that c-Myc expression is a prerequisite for effective inhibition of cell growth by the compounds and that the compounds specifically target the c-Myc/Max complex. These experiments further suggest that the effects of these compounds in vivo would be limited to those proliferating cell compartments that actually express c-Myc, such as bone marrow and GI tract cells.

Example 4

Figures 5A, 5B:
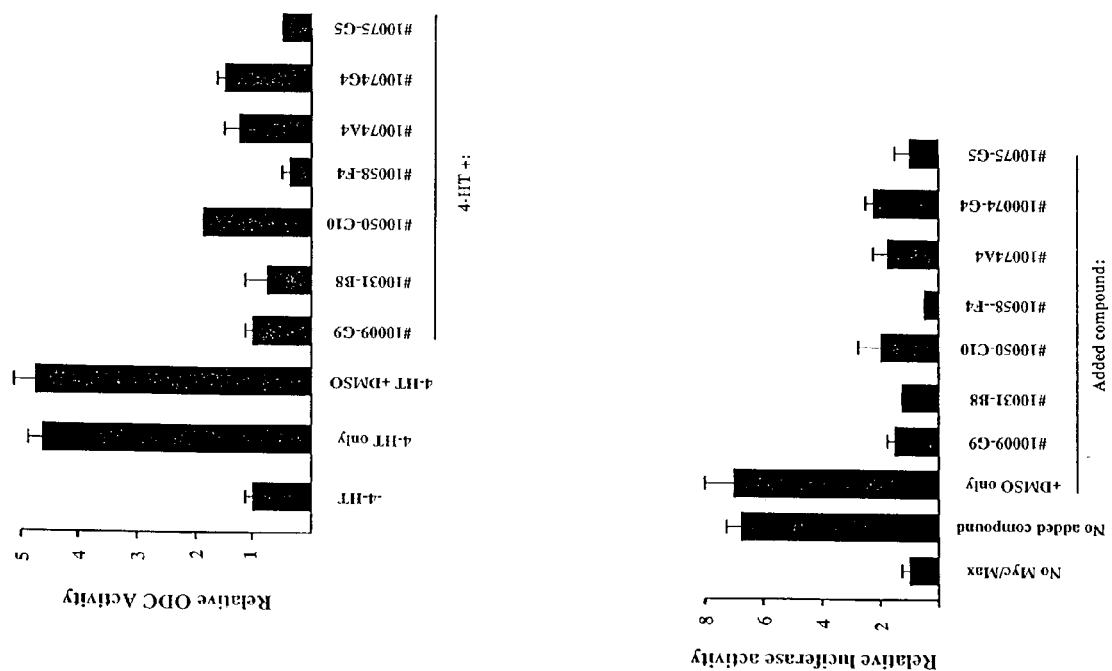
FIG. 5A is a graph showing the inhibition of ornithine decarboxylase in cells treated with the seven Myc-Max-specific compounds.
FIG. 5B is a graph showing inhibition of expression, of a Myc-responsive luciferase construct by the Seven Myc-Max-specific compounds.

Inhibition of c-Myc Target Gene Expression and Cell Cycle Progression by Myc-Max-Specific Compounds A large number of both positively and negatively regulated c-Myc target genes have been identified to date, with many of these encoding proteins involved in cell cycle control, growth and metabolism, extracellular matrix formation, and apoptosis (Dang, 1999; Oster et al., 2002). The ornithine decarboxylase (ODC) gene is a direct and positive c-Myc target that has been identified in independent microarray searches for c-Myc-regulated genes (Bello-Fernandez C., Packham G. and Cleveland J. L. (1993), *Proc. Natl. Acad. Sci. USA,* 90:7804–7809; H. A. Coller et al. (2000), *Proc. Natl. Acad. Sci. USA* 97: 3260; R. C. O'Hagan et al. (2000), *Nature Genetics* 24:113). Upregulation of ODC requires the obligate binding of c-Myc-Max heterodimers to two c-Myc-binding sites located within the first intron of the gene (Bello-Fernandez et al., 1993). Like c-Myc, ectopic overexpression of ODC is also transforming, proapoptotic, and promotes cell cycle progression (Bowlin T L, McKnown B and Sunkara P (1986), *Cell. Immunol.,* 98:341–350;

Auvinen M, Paasinen A, Anderson L C and Holtta E (1992), *Nature,* 360:355–358 and Packham and Cleveland, 1994). It was therefore determined whether any of the Myc-Max compounds could prevent the c-Myc-mediated induction of endogenous ODC. For these experiments, Rat1a cells harboring a c-Myc-estrogen receptor fusion protein (MycERt) that exists in an inactive form in the absence of the estrogen analog 4-hydroxytamoxifen (4-HT) (T. D. Littlewood, et al. (1995), *Nucl. Acids. Res.* 25:1686 and Yin et al., 2001) were utilized. As seen in FIG. 5A, the addition of 4-HT to Rat1a-MycER cells resulted in a nearly fivefold upregulation of ODC that was not significantly affected by the addition of DMSO vehicle alone. In contrast, each of the Myc-Max-specific compounds inhibited by 80–94% the ability of activated MycERt to upregulate ODC. Similar results were obtained with Rat1a-c-Myc cells (not shown).

FIG. 5A shows inhibition of ODC enzyme induction by Myc-Max specific compounds. Rat1a-MycER cells (Yin et al., 2001) were grown to approximately 75% confluency and then treated with 250 nm 4-HT in complete medium for 16 h. Where indicated, 4-HT and Myc-Max specific compounds were added simultaneously at the concentrations shown in FIG. 4. Cells were harvested 16 h later after confirming that >95% of the cells remained viable. Equivalent amounts of protein (50 µg) were assayed for ODC as previously described (Zhang et al. 1997; Nesbit et al., 2000). The results show the average of triplicate determinations ±1 s.e.

In a more general test for the efficacy and specificity of each compound, we performed transient transfection experiments in C3H10T1/2 cells utilizing c-Myc and Max expression vectors and a reporter construct consisting of a luciferase cassette under the control of an adenoviral E1b promoter juxtaposed to three tandemly arranged c-Myc-binding sites (Zhang et al., 1997). At 16 h after transfection, each of the Myc-Max compounds was then added to the cells for an additional 48 h. Cells were harvested and lysates were adjusted to take into account differences in β-galactosidase activity. Luciferase assays were then performed on the normalized samples as previously described (Zhang et al., 1997; Yin et al., 1999a). As seen in FIG. 5B, each of the compounds significantly inhibited the c-Myc-Max mediated induction of luciferase activity.

In FIG. 5B C3H10T1/2, cells were transiently transfected with equal amounts of c-Myc and Max expression vectors together with the Myc-responsive 3Xmyc-E1b-luciferase reporter (lanes 2–10). After 16 h, later, each of the indicated compounds was added at the concentrations indicated in FIG. 4 for an additional 48 h at which time cell lysates were prepared and assayed for b-galactosidase and luciferase. In the first lane, empty pSVL parental vector was substituted for the Myc and Max expression plasmids. The results show the average of triplicate determinations ±1 s.e.

Figure 5C:
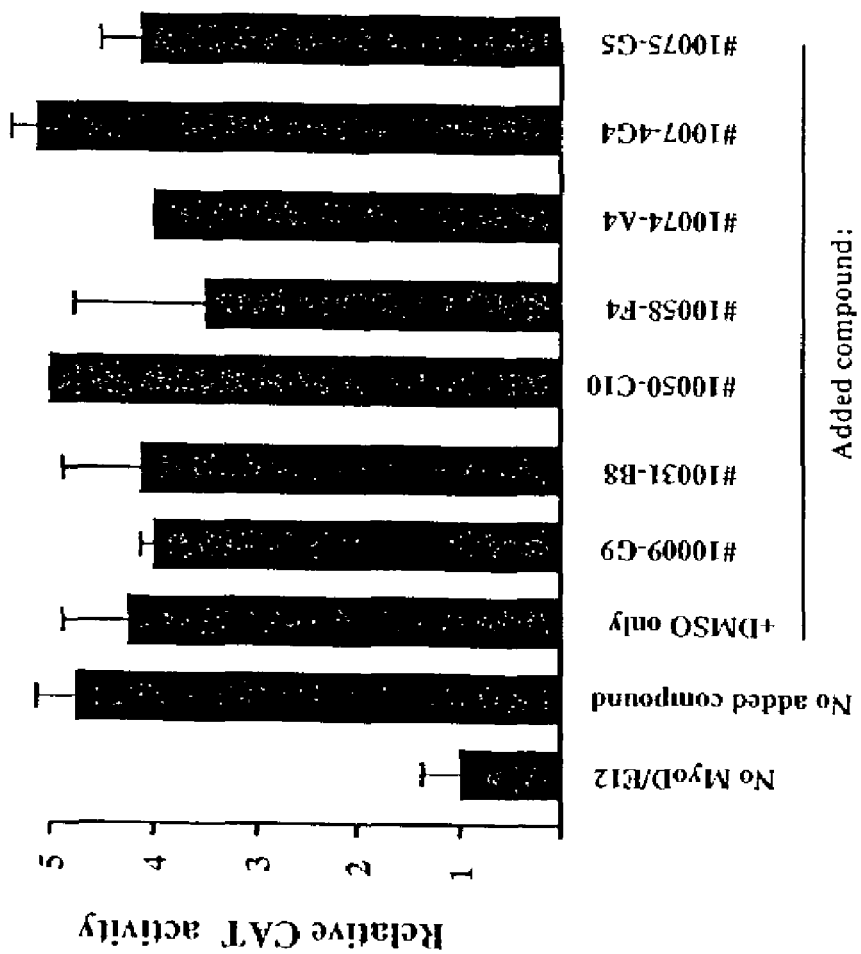
FIG. 5C is a graph showing a control experiment in which the same cells described in relation to FIG. 5B were transfected with Myc and E12 expression vectors and a chloramphenicol acetyl transferase (CAT) reporter construct under the control of the MycD-responsive muscle creatine kinase promoter. The lack of significant inhibition by any of the compounds indicates their specificity for those genes under the control of c-Myc.

In control experiments, the same cells were transfected with MyoD and E12 expression vectors and a CAT reporter construct under the control of the MyoD responsive muscle creatine kinase promoter (p3300-CAT; Van Antwerp et al., 1992). As seen in FIG. 5C, the concentrations of the compound that were effective in inhibiting c-Myc-Max-mediated transactivation in the previous two experiments had no effect on transactivation mediated by MyoD-E12. Together with the results shown in FIGS. 5A and 5B, these results extend those shown in FIG. 3 to mammalian cells and demonstrate that the specificity for c-Myc-Max-induced targets is maintained.

In FIG. 5C, C3H10T1/2 cells were transiently transfected with equal amounts of MyoD and E12 expression vectors together with the MyoD-responsive p3300MCK-CAT reporter (Van Antwerp et al., 1992) (lanes 2–10). After 16 h, later, each of the indicated compounds was added as described above. Cell lysates were prepared 48 h later and assayed for β-galactosidase and CAT in triplicate. In the first lane, empty pRcCMV vector was substituted for the MyoD and E12 expression vectors In contrast to c-Myc's promotion of cell cycle progression, its inhibition halts this process and results in an accumulation of cells in G0/G1 (Freytag S. O. (1988), *Mol. Cell. Biol.,* 8:1614–1624; Prochownik et al., 1988 and deAlboran et al., 2001). Therefore, it was asked whether any of the above compounds could affect the cell cycle profiles of otherwise actively proliferating cells. Rat1a-c-Myc cells were plated at low concentrations and grown for 2 additional days until attaining approximately 30% confluency. The cells were then re-fed with fresh medium alone, medium containing DMSO only, or medium containing each of the Myc-Max-specific compounds. After 24 h, cells were harvested and cell cycle profiles were generated by flow cytometry following propidium iodide staining (Yin et al., 2001). As seen in Table 1, the addition of DMSO alone did not noticeably affect the cell cycle profiles. In contrast, all of the compounds tested caused significant increases in the fraction of the G0/G1 population.

TABLE 1

Effect of Myc-Max-specific compounds on cell cycle profiles

| | % of cells in | | |
|---|---|---|---|
| Addition | G0/G1 | S | G2/M |
| None | 36.8 | 46.1 | 17.1 |
| DMSO only | 35.1 | 49.9 | 15.0 |
| #10009 | 66.3 | 23.1 | 10.6 |
| #10031 | 60.9 | 33.9 | 5.2 |
| #10050 | 58.7 | 29.6 | 11.7 |
| #10058 | 62.6 | 23.7 | 13.7 |
| #10074A4 | 68.7 | 21.5 | 9.8 |
| #10074G4 | 53.9 | 38.7 | 7.4 |
| #10075 | 65.1 | 24.2 | 10.7 |

Rat1a-c-Myc cells were grown for 2 days to approximately 30% confluency at which time fresh medium containing the indicated compounds was added. The concentration of each compound was as indicated in the legend to FIG. 4. After 24 h, later, cells were harvested and cell cycle parameters were determined on propidium iodide-stained nuclei as previously determined (Yin et al., 2001). Numbers shown represent the averages of triplicate samples. Standard errors ranged from 2.2–6.7%. In all cases, the proportion of apoptotic cells (with subdiploid DNA) content was <5%, thus confirming the results of trypan blue staining.

Taken together, the above experiments indicate that each of the Myc-Max-specific compounds is able to inhibit specifically the induction of defined c-Myc target genes as well as other presumed c-Myc targets whose products promote cell cycle progression.

Example 5

Inhibition of Tumorigenicity by Myc-Max-Specific Compounds

Rat1a-c-Myc cells form rapidly growing tumors in nude mice (Yin et al., 1999b). Therefore, we tested four of the Myc-Max-specific compounds to determine whether, as suggested by the in vitro experiments depicted in FIG. 4, they could also inhibit in vivo tumor growth as well (FIG. 6). Rat1a-c-Myc cells were therefore exposed to the indicated Myc-Max-specific compounds for 3 days at the concentrations shown in FIG. 4. Trypan Blue determinations of viability and TUNEL assays performed at the end of this period showed that >90% of the cells in each cell line remained alive. These cells were then inoculated into nude mice and monitored for tumor formation. Rat1a-c-Myc cells that had been incubated for 3 days in DMSO vehicle only served as a positive control. As seen in FIG. 5, all four compounds significantly reduced tumor growth.

Figure 6A:
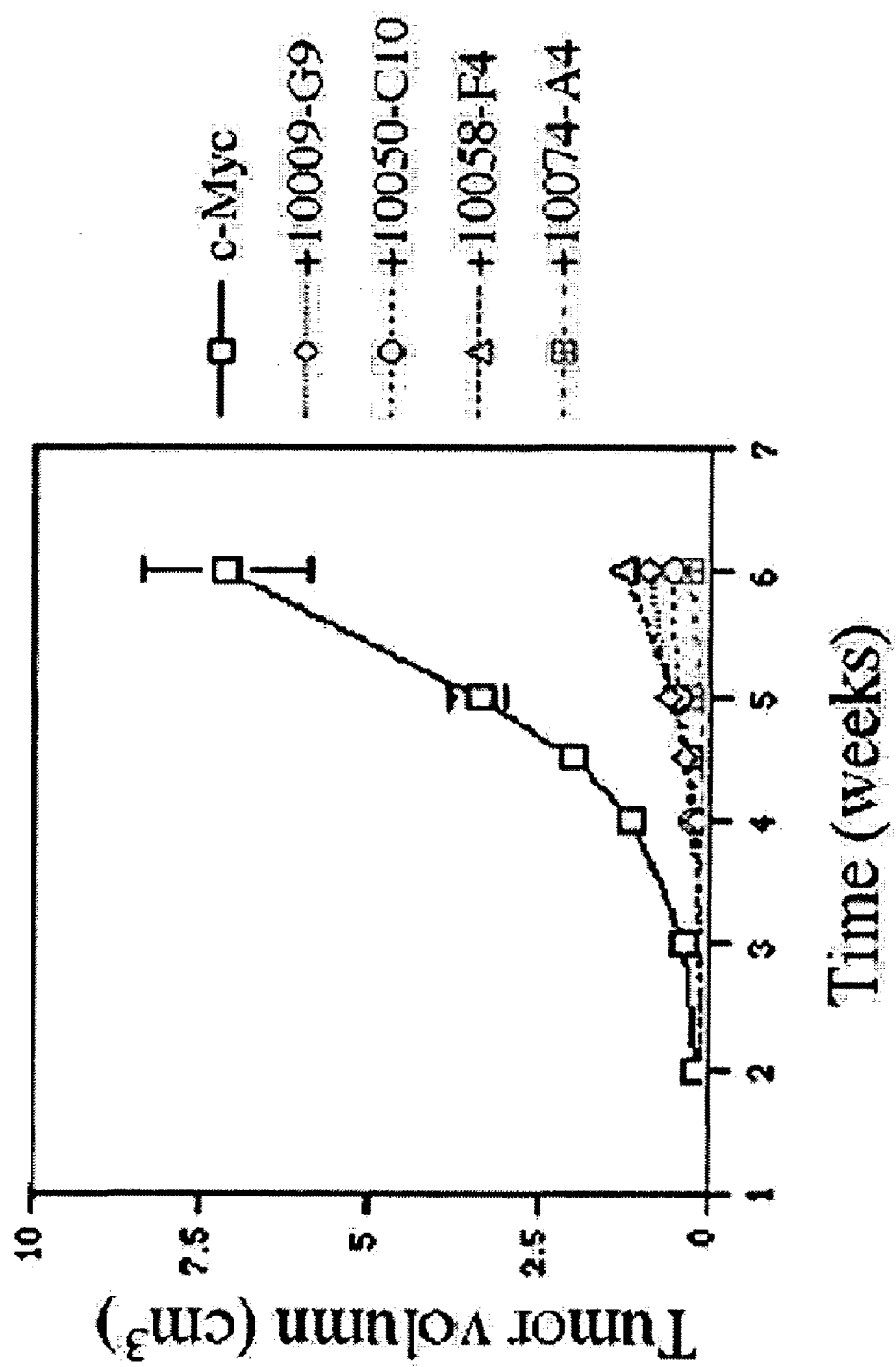
FIG. 6A is a graph showing the inhibition of in vivo tumor growth by the four compounds 10009-G9, 10050-C10, 10058-F4 and 10074-A4, which are depicted structurally in FIG. 6B.
Figure 6B:
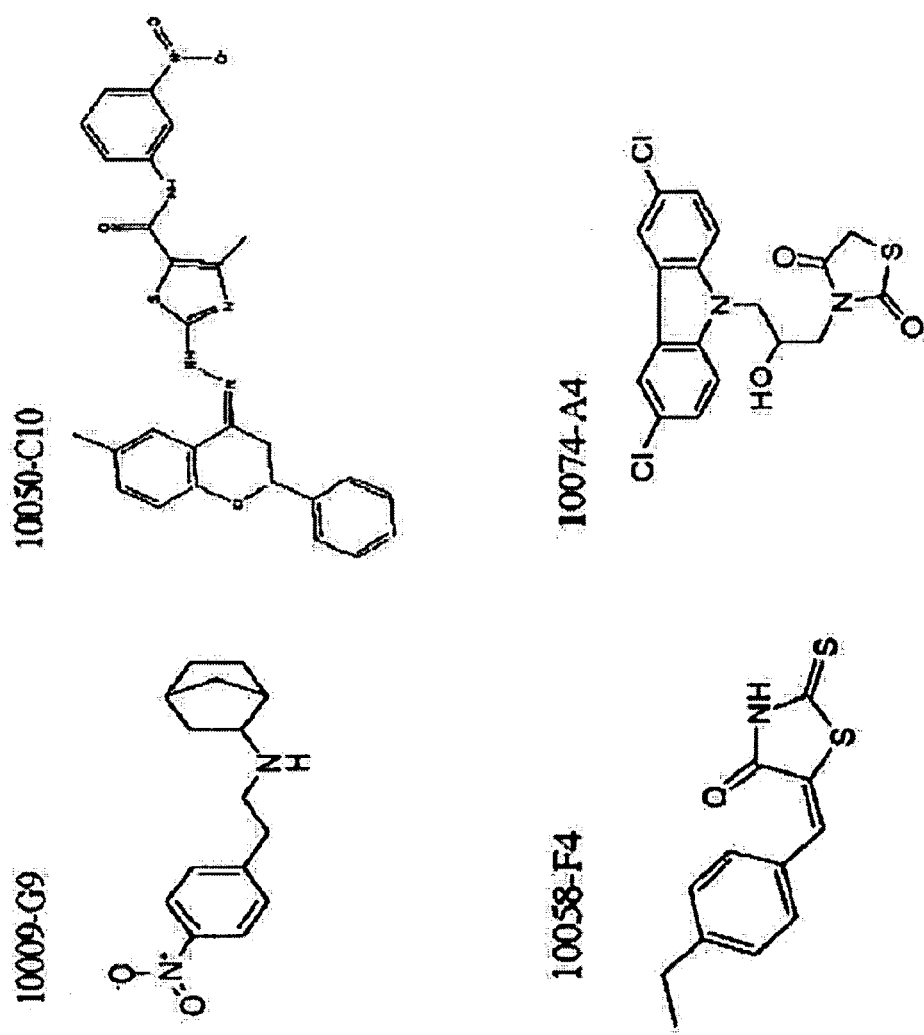

FIG. 6A shows inhibition of in vivo tumor growth. Rat1a-c-Myc cells were exposed to the indicated Myc-Max-specific compounds for 3 days at the concentrations shown in FIG. 4, and then inoculated subcutaneously into the flanks of nude mice (five animals per group). Based on trypan blue staining, >95% of the inoculated cells were viable at the time of inoculation. Tumor growth was monitored and recorded weekly. Each point indicates the average tumor volume among the groups ±1 s.e. FIG. 6B shows structures of the compounds tested in FIG. 6A.

Example 6

In Silico Data Mining for Functional Analogs of Compound 10075-G5

The seven "lead" compounds described above as being highly specific for c-Myc-Max are potent growth inhibitors of c-Myc-expressing cells. Nevertheless, identification of structural and functional analogs could lead to the discovery of active compounds that might be preferable to lead compounds.

As an example, the lead compound listed as #10075-G5, above, was used as the structural basis for an in silico screening for analogs using the software package "Hit-2 Lead" (Chembridge). In this screening, approximately 310,000 compounds available from Chembridge were reviewed to find the most related structures. The structure of lead compound 10075-G5 is provided in FIG. 7A. The software readily identified approximately 10 compounds, several of which are shown in FIGS. 7B–7E.

"Second generation" compounds such as those shown in FIGS. 7B–7E, as well as those related to other lead compounds described above will be compared in the various assays described above. Those second generation structural analogs can be members of the Chembridge chemical library or can be synthesized by a variety of methods as are known in the art.

We claim:

1. A method of inhibiting growth or proliferation of a cancer cell, comprising contacting the cell with an amount of a compound that interferes with c-Myc and Max association effective to inhibit growth or proliferation of the cell, wherein the compound is selected from the group consisting of:
   (a) Bicyclo[2.2.1]hept-2-yl-[2-(4-nitro-phenyl)-ethyl]-amine;
   (b) 4-Methyl-2- [N'-(6-methyl-2-phenyl-chroman-4-ylidene)-hydrazino]-thiazole-5-carboxylic acid (3-nitro-phenyl)-amide;
   (c) 5-(4-Ethyl-benzylidene)-2-thioxo-thiazolidin-4-one;
   (d) 3-[3-(3,6-Dichloro-carbazol-9-yl)-2-hydroxy-propyl]-thiazolidine-2,4-dione;
   (e) Biphenyl-2-yl-(7-nitro-benzo[1,2,5]oxadiazol-4-yl)-amine;
   (f) 1-(3-Chloro-phenyl)-3-diethylamino-pyrrolidine-2,5-dione; and
   (g) 1-[2,5-dioxo-1-(4-propoxy-phenyl)-pyrrolidin-3-yl]-piperidine-4-carboxylic acid, or a pharmaceutically acceptable salt thereof.

2. The method of claim 1, wherein the cell is contacted with the compound in a concentration range of from about 0.01 µM to about 100 µM.

3. The method of claim 2, wherein the concentration range is from 1.0 µM to about 75 µM.

4. A composition comprising a compound selected from the group consisting of: (a) Bicyclo[2.2.1]hept-2-yl-[2-(4-nitro-phenyl)-ethyl]-amine; (b) 4-Methyl-2-[N'-(6-methyl-2-phenyl-chroman-4-ylidene)-hydrazino]-thiazole-5-carboxylic acid (3-nitro-phenyl)-amide; (c) 5-(4-Ethyl-benzylidene)-2-thioxo-thiazolidin-4-one; (d) 3-[3-(3,6-Dichloro-carbazol-9-yl)-2-hydroxy-propyl]-thiazolidine-2, 4-dione; (e) Biphenyl-2-yl-(7-nitro-benzo[1,2,5]oxadiazol-4-yl)-amine; (f) 1-(3-Chloro-phenyl)-3-diethylamino-pyrrolidine-2,5-dione; and (g)1-[2,5-dioxo-1-(4-propoxy-phenyl)-pyrrolidin-3-yl]-piperidine-4-carboxylic acid, or a pharmaceutically acceptable salt thereof, in an amount effective to inhibit growth or proliferation of a cancer cell in a patient; and ii) a pharmaceutically acceptable excipient.

5. The composition of claim 4, wherein the excipient is a solubilizing agent.

6. The composition of claim 5, wherein the solubilizing agent is one of a polyoxyethylene-substituted vegetable oil and a cyclodextrin.

7. The composition of claim 6, wherein the vegetable oil is castor oil.

8. The composition of claim 5, wherein the solubilizing agent is an emulsifier.

9. The composition of claim 4, wherein the compound is Bicyclo[2.2.1]hept-2-yl-[2-(4-nitro-phenyl)-ethyl]-amine or a pharmaceutically acceptable salt thereof.

10. The composition of claim 4, wherein the compound is 4-Methyl-2-[N'-(6-methyl-2-phenyl-chroman-4-ylidene)-hydrazino]-thiazole-5-carboxylic acid (3-nitro-phenyl)-amide or a pharmaceutically acceptable salt thereof.

11. The composition of claim 4, wherein the compound is 5-(4-Ethyl-benzylidene)-2-thioxo-thiazolidin-4-one or a pharmaceutically acceptable salt thereof.

12. The composition of claim 4, wherein the compound is 3-[3-(3,6-Dichlorocarbazol-9-yl)-2-hydroxy-propyl]-thiazolidine-2,4-dione or a pharmaceutically acceptable salt thereof.

13. The composition of claim 4, wherein the compound is Biphenyl-2-yl-[(1,2,5]oxadiazol-4-yl)-amine or a pharmaceutically acceptable salt thereof.

14. The composition of claim 4, wherein the compound is 1-(3-chloro-phenyl)-3-diethylamino-pyrrolidine-2,5-dione or a pharmaceutically acceptable salt thereof.

15. The composition of claim 4, wherein the compound is 1-[2,5-dioxo-1-(4-propoxy-phenyl)-pyrrolidin-3-yl]-piperidine-4-carboxylic acid or a pharmaceutically acceptable salt thereof.

16. A method of inhibiting growth or proliferation of a cancer cell in a patient, comprising administering to the patient in need thereof an amount of a compound that interferes with c-Myc and Max association effective to inhibit growth or proliferation of the cell, wherein the compound is selected from the group consisting of: (a) Bicyclo[2.2.1]hept-2-yl-[2-(4-nitro-phenyl)-ethyl]-amine; (b) 4-Methyl-2-[N'-(6-methyl-2-phenyl-chroman-4-ylidene)-hydrazino]-thiazole-5-carboxylic acid (3-nitro-phenyl)-amide; (c) 5-(4-Ethyl-benzylidene)-2-thioxo-thiazolidin-4-one; (d) 3-[3-(3,6-Dichloro-carbazol-9-yl)-2-hydroxy-propyl]-thiazolidine-2,4-dione; (e) Biphenyl-2-yl-(7-nitro-benzo[1,2,5]oxadiazol-4-yl) -amine; (f)1-(3-Chloro-phenyl)-3-diethylamino-pyrrolidine-2,5-dione; and (g) 1-[2,5-dioxo-1-(4 4-propoxy-phenyl)-pyrrolidin-3-yl]-piperidine-4-carboxylic acid, or pharmaceutically acceptable salt thereof.

17. The method of claim 16, wherein the patient is administered a dose of the compound ranging from about 1 µg per kg of patient body weight to about 1 mg per kg of patient body weight.

18. The method of claim 17, the patient is administered a range from about 100 µg per kg of patient body weight to about 1 mg per kg of patient body weight.

19. The method of claim 1, wherein the compound is Bicyclo[2.2.1]hept-2-yl-[2-(4-nitro-phenyl)-ethyl]-amine or a pharmaceutically acceptable salt thereof.

20. The method of claim 1, wherein the compound is 4-Methyl-2-[N'-(6-methyl-2-phenyl-chroman-4-ylidene)-hydrazino]-thiazole-5-carboxylic acid (3-nitro-phenyl)-amide or a pharmaceutically acceptable salt thereof.

21. The method of claim 1, wherein the compound is 5-(4-Ethyl-benzylidene)-2-thioxo-thiazolidin-4-one or a pharmaceutically acceptable salt thereof.

22. The method of claim 1, wherein the compound is 3-[3-(3,6-Dichlorocarbazol-9-yl)-2-hydroxy-propyl]-thiazolidine-2,4-dione or a pharmaceutically acceptable salt thereof.

23. The method of claim 1, wherein the compound is Biphenyl-2-yl-[(1,2,5]oxadiazol-4-yl)-amine or a pharmaceutically acceptable salt thereof.

24. The method of claim 1, wherein the compound is 1-(3-chloro-phenyl)-3-diethylamino-pyrrolidine-2,5-dione or a pharmaceutically acceptable salt thereof.

25. The method of claim 1, wherein the compound is 1-[2,5-dioxo-1-(4-propoxy-phenyl)-pyrrolidin-3-yl]-piperidine-4-carboxylic acid or a pharmaceutically acceptable salt thereof.

26. The method of claim 16, wherein the compound is Bicyclo[2.2.1]hept-2-yl-[2-(4-nitro-phenyl)-ethyl]-amine or a pharmaceutically acceptable salt thereof.

27. The method of claim 16, wherein the compound is 4-Methyl-2-[N'-(6-methyl-2-phenyl-chroman-4-ylidene)-hydrazino]-thiazole-5-carboxylic acid (3-nitro-phenyl)-amide or a pharmaceutically acceptable salt thereof.

28. The method of claim 16, wherein the compound is 5-(4-Ethyl-benzylidene)-2-thioxo-thiazolidin-4-one or a pharmaceutically acceptable salt thereof.

29. The method of claim 16, wherein the compound is 3-[3-(3,6-Dichlorocarbazol-9-yl)-2-hydroxy-propyl]-thiazolidine-2,4-dione or a pharmaceutically acceptable salt thereof.

30. The method of claim 16, wherein the compound is Biphenyl-2-yl-[(1,2,5]oxadiazol-4-yl)-amine or a pharmaceutically acceptable salt thereof.

31. The method of claim 16, wherein the compound is 1-(3-chloro-phenyl)-3-diethylamino-pyrrolidine-2,5-dione or a pharmaceutically acceptable salt thereof.

32. The method of claim 16, wherein the compound is 1-[2,5-dioxo-1-(4-propoxy-phenyl)-pyrrolidin-3-yl]-piperidine-4-carboxylic acid or a pharmaceutically acceptable salt thereof.

* * * * *

UNITED STATES PATENT AND TRADEMARK OFFICE
CERTIFICATE OF CORRECTION

| | | |
|---|---|---|
| PATENT NO. | : 7,026,343 B2 | Page 1 of 1 |
| APPLICATION NO. | : 10/459769 | |
| DATED | : April 11, 2006 | |
| INVENTOR(S) | : Prochownik et al. | |

It is certified that error appears in the above-identified patent and that said Letters Patent is hereby corrected as shown below:

The STATEMENT REGARDING FEDERAL SUPPORT on column 1, lines 15-16 should read: "This invention was made with governmental support under DOD Grant DAMD 17-00-1-0013 and National Institutes of Health Grant HL 33741. The government has certain rights in this invention.

Signed and Sealed this

Fifth Day of December, 2006

JON W. DUDAS
*Director of the United States Patent and Trademark Office*

UNITED STATES PATENT AND TRADEMARK OFFICE
CERTIFICATE OF CORRECTION

PATENT NO. : 7,026,343 B2
APPLICATION NO. : 10/459769
DATED : April 11, 2006
INVENTOR(S) : Prochownik et al.

Page 1 of 1

It is certified that error appears in the above-identified patent and that said Letters Patent is hereby corrected as shown below:

<u>In the Specification:</u>

Column 1, lines 15-16, "This work was supported by DOD Grant DAMD 17-00-1-0013 and NIH grant HL 33741." should read -- This invention was made with government support under grant no. DAAD17-00-1-0013 awarded by the Department of Defense and grant no. HL033741 awarded by the National Institutes of Health. The government has certain rights in the invention. --.

Signed and Sealed this
Second Day of July, 2013

Teresa Stanek Rea
*Acting Director of the United States Patent and Trademark Office*